United States Patent
Patton

(10) Patent No.: US 11,751,953 B2
(45) Date of Patent: Sep. 12, 2023

(54) CLOUD BASED SYSTEM CATARACT TREATMENT DATABASE AND ALGORITHM SYSTEM

(71) Applicant: Douglas Patton, Irvine, CA (US)

(72) Inventor: Douglas Patton, Irvine, CA (US)

(73) Assignee: Lensar, Inc., Orlando, FL (US)

( * ) Notice: Subject to any disclaimer, the term of this patent is extended or adjusted under 35 U.S.C. 154(b) by 505 days.

(21) Appl. No.: 16/863,905

(22) Filed: Apr. 30, 2020

(65) Prior Publication Data

US 2020/0345431 A1    Nov. 5, 2020

Related U.S. Application Data

(60) Provisional application No. 62/850,876, filed on May 21, 2019, provisional application No. 62/842,850, filed on May 3, 2019.

(51) Int. Cl.
*A61B 34/00* (2016.01)
*A61B 34/10* (2016.01)
*G06N 20/00* (2019.01)
*A61B 3/11* (2006.01)

(52) U.S. Cl.
CPC .............. *A61B 34/25* (2016.02); *A61B 3/11* (2013.01); *A61B 34/10* (2016.02); *G06N 20/00* (2019.01); *A61B 2034/105* (2016.02); *A61B 2034/256* (2016.02)

(58) Field of Classification Search
None
See application file for complete search history.

(56) References Cited

U.S. PATENT DOCUMENTS

| 4,729,373 A | 3/1988 | Peyman |
| 4,825,865 A | 5/1989 | Zelman |
| 4,946,452 A | 8/1990 | Py |

(Continued)

FOREIGN PATENT DOCUMENTS

| EP | 1666009 | 6/2006 |
| EP | 2057973 | 5/2009 |

(Continued)

OTHER PUBLICATIONS

Jul. 7, 2021, WIPO, PCT/US21/12008—Opinin and search report.

(Continued)

*Primary Examiner* — Andrew G Yang
(74) *Attorney, Agent, or Firm* — Glen P. Belvis; Belvis Law, LLC.

(57) ABSTRACT

Systems, devices and methods are provided that provide assistance in selecting appropriate interventions for treatment of disease and injury to the eye. Systems of the inventive concept provide cloud-based processing and storage of clinical and patient-specific data, which can provide treatment recommendations and projected outcomes to a practitioner using a local device. Systems, devices, and methods can generate interactive physiomechanical models of the eye of a specified individual, which are derived measurements of mechanical properties of structures of the eye. The physiomechanical model is interactive, and can be used to emulate the effects of one or more medical interventions in the eye in order to implement an optimized treatment plan for the individual.

25 Claims, 11 Drawing Sheets

Basic Workflow

(56) References Cited

U.S. PATENT DOCUMENTS

| | | |
|---|---|---|
| 5,057,098 A | 10/1991 | Zelman |
| 5,098,426 A | 3/1992 | Sklar |
| 5,139,504 A | 8/1992 | Zelman |
| 5,423,801 A | 6/1995 | Marshall |
| 5,548,352 A | 8/1996 | Dewey |
| 5,591,160 A | 1/1997 | Reynard |
| 5,651,783 A | 7/1997 | Reynard |
| 5,695,461 A | 12/1997 | Schaible |
| 5,722,970 A | 3/1998 | Colvard et al. |
| 5,741,244 A | 4/1998 | Klaas |
| 6,045,527 A | 4/2000 | Appelbaum |
| 6,391,020 B1 | 5/2002 | Kurtz |
| 6,544,254 B1 | 4/2003 | Bath |
| 6,733,491 B2 | 5/2004 | Kadziauskas |
| 6,962,583 B2 | 11/2005 | Kadziauskas |
| 7,130,835 B2 | 10/2006 | Cox |
| 7,182,759 B2 | 2/2007 | Kadziauskas |
| 8,005,947 B2 | 8/2011 | Morris |
| 8,986,290 B2 | 3/2015 | Patton |
| 9,050,171 B2 | 6/2015 | Foster |
| 9,095,415 B2 | 8/2015 | Blumenkranz et al. |
| 9,107,732 B2 | 8/2015 | Blumenkranz et al. |
| 9,259,354 B2 | 2/2016 | Horvath |
| 9,492,318 B2 | 11/2016 | Rockley et al. |
| 10,709,610 B2 | 7/2020 | Morley et al. |
| 2002/0075451 A1 | 6/2002 | Ruiz |
| 2003/0050629 A1 | 3/2003 | Kadziauskas |
| 2003/0073984 A1 | 4/2003 | Maeda |
| 2004/0034340 A1 | 2/2004 | Biscup |
| 2006/0115135 A1* | 6/2006 | Dehmeshki ............ G16H 30/40 |
| | | 382/128 |
| 2007/0027470 A1 | 2/2007 | Dodick |
| 2007/0073905 A1* | 3/2007 | Cynthia ................. G16H 50/50 |
| | | 710/1 |
| 2007/0161972 A1 | 7/2007 | Felberg |
| 2007/0237620 A1 | 10/2007 | Muhlhoff |
| 2008/0004608 A1 | 1/2008 | Dacquay |
| 2008/0013048 A1 | 1/2008 | Gaida |
| 2008/0071254 A1 | 3/2008 | Lummis |
| 2009/0137991 A1 | 5/2009 | Kurtz |
| 2009/0247999 A1 | 10/2009 | Tuan |
| 2009/0271155 A1* | 10/2009 | Dupps, Jr. ................ G16B 5/00 |
| | | 703/2 |
| 2010/0191100 A1* | 7/2010 | Anderson ............... G06T 7/246 |
| | | 600/424 |
| 2011/0022035 A1 | 1/2011 | Porter |
| 2011/0224657 A1* | 9/2011 | Stevens ................... A61F 9/008 |
| | | 606/5 |
| 2011/0288470 A1 | 11/2011 | Boukhny |
| 2013/0023864 A1 | 1/2013 | Blumenkranz |
| 2013/0090636 A1 | 4/2013 | Patton |
| 2014/0052113 A1 | 2/2014 | Kuehnert |
| 2014/0104576 A1 | 4/2014 | Bor et al. |
| 2014/0107634 A1 | 4/2014 | Voglar |
| 2014/0364870 A1 | 12/2014 | Alvarez et al. |
| 2015/0190281 A1 | 7/2015 | Patton |
| 2015/0255004 A1* | 9/2015 | Manzke ............... G09B 23/285 |
| | | 434/267 |
| 2016/0045367 A1* | 2/2016 | Horvath ............. A61F 9/00825 |
| | | 606/6 |
| 2016/0089269 A1 | 3/2016 | Horvath |
| 2016/0302915 A1* | 10/2016 | Sayegh .................. A61F 9/007 |
| 2017/0000645 A1 | 1/2017 | Summers et al. |
| 2017/0000647 A1 | 1/2017 | Schuele et al. |
| 2017/0056245 A1 | 3/2017 | Rockley et al. |
| 2017/0119249 A1 | 5/2017 | Gunn |
| 2017/0119578 A1 | 5/2017 | Rockley et al. |
| 2017/0246471 A1* | 8/2017 | Lopath ................. A61B 3/1005 |
| 2017/0290703 A1 | 10/2017 | Teuma et al. |
| 2017/0340483 A1 | 11/2017 | Rill et al. |
| 2018/0028355 A1 | 2/2018 | Raksi |
| 2018/0055581 A1* | 3/2018 | Papac .................... A61B 34/25 |
| 2018/0085256 A1 | 3/2018 | Gray et al. |
| 2018/0161051 A1 | 6/2018 | Humayun |
| 2018/0168859 A1 | 6/2018 | Bischoff et al. |
| 2018/0185043 A1 | 7/2018 | Humayun |
| 2018/0206717 A1 | 7/2018 | Ramesh Kumar et al. |
| 2018/0250090 A1 | 9/2018 | Patton |
| 2019/0083308 A1 | 3/2019 | Rathjen |
| 2019/0096933 A1 | 3/2019 | Kido et al. |
| 2019/0365567 A1 | 12/2019 | Balkenbush et al. |
| 2020/0258599 A1* | 8/2020 | Clark ..................... G06N 20/00 |
| 2021/0259880 A1 | 8/2021 | Newton et al. |
| 2021/0259881 A1 | 8/2021 | Gray et al. |
| 2021/0298955 A1 | 9/2021 | McWhirter et al. |
| 2021/0378864 A1 | 12/2021 | Teuma et al. |

FOREIGN PATENT DOCUMENTS

| | | |
|---|---|---|
| JP | 2015 02964 | 2/2015 |
| WO | WO1992017138 | 10/1992 |
| WO | WO1997022304 | 6/1997 |
| WO | WO1998012973 | 4/1998 |
| WO | WO 1999065405 | 12/1999 |
| WO | WO2006074469 | 7/2006 |
| WO | WO200903935 | 3/2009 |
| WO | WO2009061758 | 5/2009 |
| WO | WO2012047492 | 4/2012 |
| WO | WO 2013057098 | 4/2013 |
| WO | WO2013126653 | 8/2013 |
| WO | WO2014201165 | 12/2014 |

OTHER PUBLICATIONS

Apr. 6, 2021, WIPO, PCT/US21/12009—Opinin and search report.
May 25, 2021, WIPO, PCT/US21/12010—Opinin and search report.
Jun. 25, 2021, WIPO, PCT/US21/12011—Opinin and search report.
Sep. 28, 2020, EIPO, PCT/US20/30823 Opinion.
Sep. 28, 2020, EIPO, PCT/US20/30823 Search.

* cited by examiner

CLOUD BASED SYSTEM CATARACT TREATMENT DATABASE AND ALGORITHM SYSTEM

This application claims the benefit of U.S. Provisional Patent Application No. 62/850,876 filed on May 21, 2019, U.S. Provisional Patent Application No. 62/842,850 filed on May 3, 2019. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is computer-aided surgery, in particular ophthalmic surgery.

BACKGROUND

This Background section is intended to introduce various aspects of the art, which may be associated with embodiments of the present inventions. Thus, the forgoing discussion in this section provides a framework for better understanding the present inventions, and is not to be viewed as an admission of prior art.

It should be understood that the use of headings in this specification is for the purpose of clarity, and is not limiting in any way. Thus, the processes and disclosures described under a heading should be read in context with the entirely of this specification, including the various examples. The use of headings in this specification should not limit the scope of protection afford the present inventions.

Currently, success in surgical interventions in the eye such as LASIK, PRK, lens removal, and artificial lens placement lies largely in the skill and experience of the individual surgeon and their ability to adapt an ongoing procedure as normal variations within the eye and surgical complications become apparent. As a result less than optimal outcomes and the need for additional 'touch up' procedures occur at a higher than desirable rate.

Computer-based systems have been developed to improve patient outcomes by facilitating patient tracking and consultation between practitioners. For example, U.S. Pat. No. 9,700,292, to Nawana et al., describes a computerized system that tracks patients from initial onset, diagnosis, treatment, recovery, and outcome. The described system, which is primarily directed to orthopedics, can provide recommendations for diagnosis and treatment based on stored patient data and information provided by practitioners. These recommendations are based on historical data. As such, accuracy of the projected outcomes is necessarily limited by the breadth of the stored data.

One approach to addressing a lack of relevant historical clinical data is to provide a realistic model that emulates nature sufficiently to accurately predict the impact of medical intervention. United States Patent Application Publication No. US 2003/0208190 (to Roberts et al.) describes evaluating results of measurement made prior to and following creation of a corneal flap to generate a biomechanical model of the eye, which is subsequently used to generate an ablation algorithm and predict surgical outcome. This approach, however, requires a degree of surgical intervention on the eye prior to generation of a predictive model.

United States Patent Application Publication No. US 2011/0208172 (to Youssefi et al.) describes a system that makes ongoing measurements of corneal shape/thickness at multiple locations during laser ablation, and alerts the surgeon if the desired shape is not achieved. The surgeon can then make adjustments to the ablation procedure. Such a method, however, relies on the surgeon's individual experience to provide prediction of the effects of such adjustments. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

European Patent No. EP1613253 (to Matthaus et al.) describes an expert system that utilizes inputted patient-specific information to recommend from among a number of stored ophthalmological treatment plans those which are best suited for the individual patient. The surgeon then selects from among these treatment plans based upon their individual experience and preferences. Such a system, however, is not truly predictive of outcome.

United States Patent Application Publication No. 2007/0073905 (to Roberts et al.) describes a trained expert system that utilizes stored correlations between pre-operative and intra-operative measurements of various characteristics of the eyes of previous patients with their respective patient-specific outcomes to make recommendations to the ophthalmic surgeon based on similar measurements from their specific patient. The results from such expert systems, however, are highly dependent on the available dataset. Such a system may not be adequately predictive for a patient whose measurements fall outside the range of that encompassed by stored dataset.

Recently, attempts have been made to generate in numero biomechanical models of parts of the body that are capable of simulating certain functional aspects. For example, International Patent Application Publication No. WO 2019/072875 (to Deleu et al.) describes generation of such a model for the foot and ankle based on measurements of bones and soft tissues. The model is then used to emulate the foot and ankle at rest and in dynamic motion. Data derived from this emulation is used to guide the orthopedist in diagnosis and determination of suitable treatment strategies, and to emulate the effects of simulated treatment applied to the model. Similar in numero biomechanical models have also been proposed for elements of the cardiovascular system (e.g. International Patent Application Publication No. WO 2018/108276, to Dahl et al. and International Patent Application Publication No. WO 2018/057529, to Sanders et al.) and vascular elements of the brain (e.g. United States Patent Application Publication No. US 2018/0098814, to Avisar).

U.S. Pat. No. 10,181,007 describes using a finite element model to generate a "biomechanical" model of the cornea for use in optimizing LASIK procedures. The method derives a finite element model based on measurements of an individual cornea and intraocular pressure, assigning permeability values to different regions of the cornea based on these measurements. These permeability values represent the ability of fluid to move into and out of the cornea in as a result of intraocular pressure. Simulation of alterations to the cornea modifies these permeability values, resulting of calculation of a modified corneal configuration under the influence of intraocular pressure. The use of sigmoidal functions to model changes in mechanical properties of the cornea in such models, however, is not able to readily accommodate steep gradients or sudden transitions between physical properties, which are a common feature of anatomy. Studer et al (Journal of Refractive Surgery 31(7): 480-486 2015), has noted a lack of predictive value for this algorithmic approach for some procedures. This is thought to be due, at least in part, to failing to account for certain anatomical features of the eye.

Thus, there is still a need for a biomechanical or physiomechanical model of the human eye that is useful for the accurate emulation of surgical ophthalmic interventions.

SUMMARY OF THE INVENTION

The inventive subject matter provides systems, devices, and methods in which provide cloud-based collaborative and computer assisted treatment methods for use in optimizing ophthalmic procedures utilizing femtosecond laser-mediated incisions and/or phacoemulsification, for example in surgeries for removal of the natural lens in treatment of cataract. Such systems and methods utilize one or more physiomechanical models based on mechanical properties of the eye and/or structures of a patient's eye are utilized to model the effects of medical interventions on the specific patient. This modeling allows a user to develop an optimized treatment plan and to assess the probability of subsequent complications.

One embodiment of the inventive concept is a system for assisting a user in performance of an ophthalmic surgery on an eye of a patient, which includes a user interface communicatively coupled to an input/output interface (e.g. a web page) and configured to communicate with a user device; a database that includes a patient database, a clinical database, and a procedure database, where the database is communicatively coupled to the input/output interface; and a processor communicatively coupled to the input/output interface and the database. The processor includes an algorithm providing a physiomechanical model of the eye or a portion of the eye, and at least one of the input/output interface, the database, and the processor are cloud-based. In some embodiments the input/output interface includes a planning module and/or a treatment module. The database can also include a practitioner database and/or an instrument database. The processor can include a machine learning algorithm configured to correlate data from the clinical database with data from the patient database, and to provide a treatment recommendation via the input/output interface. In a preferred embodiment the input/output interface, the database, and the processor are cloud-based.

Another embodiment of the inventive concept is a method of assisting a user in performing an ophthalmic surgery by accessing a planning module of an input/output interface (e.g. a web page) that is communicatively coupled to a database and a processor, where the input/output interface includes an algorithm assist, and where the database includes a patient database, a clinical database, and a procedure database; inputting a desired outcome from the ophthalmic surgery via the input/output interface; determining a recommended procedure using a machine learning algorithm of the processor and data from the patient, clinical, and procedure databases; and transmitting the recommended procedure to the input/output interface. At least one of the input/output interface, the database, and the processor are cloud-based. In some embodiments a physiomechanical model of the eye or a portion thereof is generated, and can be used to input the desired outcome and/or display the recommended procedure to the user. The database can include a practitioner database and/or an instrument database, and the recommended procedure can be determined in part by data from the practitioner database and/or the instrument database.

In some embodiments a probable outcome of the recommended procedure is transmitted to the input/output interface. If the probable outcome is acceptable the recommended procedure can be transferred to a treatment module of the input/output interface. If the probable outcome is not acceptable, a modification to the recommended procedure can be inputted to generate revised procedure and a revised outcome. This outcome can be transmitted to the input/output interface, and if acceptable the revised procedure can be transmitted to the input/output interface.

One embodiment of the inventive concept is a method of assisting a user in performance of an ophthalmic surgery on an eye of a patient, by physically characterizing the eye to determine at least a first density and at least a first dimension of a structure of the eye, applying the determined density(ies) and dimension(s) to derive a physiomechanical model of the structure of the eye, receiving from the user a selection of a selected procedure, applying the selected procedure to the physiomechanical model to predict an effect of applying the selected procedure to the structure of the eye, and providing the user (e.g. surgeon or a medical technician) with a representation of the predicted effect of the selected procedure when applied to the structure of the eye. The representation can be one or more of tabular data, a three dimensional representation, a probability of successful or satisfactory outcome, and a recommendation of an alternative procedure. In some embodiments the method includes applying the selected procedure to the patient's eye. Suitable procedures include a femtosecond laser procedure, a YAG laser procedure, a phacoemulsification, an application of a vitrectomy blade, an intraocular aspiration, a placement of an intraocular lens, and a corneal flap cut.

The physiomechanical model is derived from a mechanical property of the eye. The mechanical property can be one or more of Young's modulus, stress/strain modulus of elasticity, Poisson's ratio, density, hardness, ductility, and results of finite element analysis of an eye structure under compression, tension, torsion, and shear.

The representation of the predicted effect of the applied procedure can derived from structural analysis of alteration of the mechanical property by the selected procedure. Alternatively, the representation of the predicated effect can be derived from minimization of a calculated strain or static energy following application of the selected procedure, wherein the calculated strain or static energy is derived from the mechanical property. In other embodiments the representation of the predicted effect of the applied procedure is derived from a combination of these.

In some embodiments of the inventive concept additional data for use in generating the physiomechanical model can be gathered and used to generate the physiomechanical model. Suitable data includes corneal acoustic response or ultrasound data, topographic data, pachymetric data, elevation data, corneal thickness data, corneal curvature data, wave front data, intraocular pressure data, peripheral stromal thickness data, patient age, patient gender, duration of contact lens use, prior surgical intervention, response to prior surgical intervention, and/or yield point of the cornea.

In some embodiments the selected procedure can be adjusted to generate a modified procedure, and the physiomechanical model used to predict effects of applying the modified procedure to the eye. Such adjustments can include one or more of (a) the amount of laser energy applied, (b) the depth of penetration of an ablation or an incision, and (c) the pattern of the ablation or the incision applied to the eye. In some embodiments series of candidate procedures and to the physiomechanical model to identify an optimal procedure.

In some embodiments the predicted effect on the structure of the eye provides a modified eye structure, and calculated physical characteristics of this modified eye structure can be utilized to generate a second physiomechanical model that represents of this modified eye structure. This second physiomechanical model can utilized to evaluate the effect of an additional selected procedure on the modified eye structure.

Another embodiments of the inventive concept is a method of phacoemulsification of an eye lens by physically characterizing the eye to determine at least a first density and at least a first dimension of a structure of the lens, applying the determined density(ies) and dimension(s) to derive a first physiomechanical model of the structure of the lens, identifying to a user a set of phacoemulsification procedures, receiving from the user a selection of a selected phacoemulsification procedure from within the set, using the first physiomechanical model to predict one or more effects of applying the selected phacoemulsification procedure to the eye, and applying the selected phacoemulsification procedure to the eye. The first physiomechanical model is derived from a mechanical property of the lens. Such embodiments can include additional steps of providing an artificial lens having at least a first haptic, using the physiomechanical model to identify a preferred position of the first haptic in a cavity formed at least in part by the phacoemulsification procedure, and positioning the artificial lens into the cavity such that the haptic is approximated at a preferred position. In some embodiments the eye is re-scanned following the selected phacoemulsification procedure to determine second densities and second dimensions. The first physiomechanical model is then modified using the second densities and second dimensions to generate a second physiomechanical model, which is in turn used to determine the probability of an complication of either of the phacoemulsification procedure (such as rupture of the capsular bag) or positioning of the artificial lens (such an incorrect post-surgical positioning of the lens).

Another embodiment of the inventive concept is a method of femtosecond laser treatment of an eye by physically characterizing the eye to determine at least a first density and at least a first dimension of a structure of the eye, applying the determined density(ies) and dimension(s) to derive a first physiomechanical model of the structure of the eye, identifying to a user a set of femtosecond laser procedures, receiving from the user a selection of a selected femtosecond laser procedure from within the set, using the first physiomechanical model to predict effect of applying the selected femtosecond laser procedure to the eye, applying the selected femtosecond laser procedure to the eye, re-characterizing the eye to determine modified densities and modified dimensions, modifying the first physiomechanical model using the modified densities and modified dimensions to generate a second physiomechanical model, using the second physiomechanical model to determine an amount of lens segmentation, and utilizing the amount of lens segmentation to propose a preferred phacoemulsification procedure.

Another embodiment of the inventive concept is a laser system that includes a femtosecond laser configured and maneuverable for delivering a femtosecond laser beam to an eye and a modeling system having a modeling engine and/or a patient data base. The patient data base is configured to receive a density characterization of a structure of the eye and a dimensional characterization of the structure of the eye. Such a system can include a graphic user interface (GUI) configured to receive an input from a user and to display an output from the modeling system. Such an input includes a selected procedure.

In some embodiments of these systems the modeling system is configured to derive a physiomechanical model representation of a structure of an eye that is based upon density characterization of the structure of the eye received from a patient data base, a determined dimensional characterization of the structure of the eye received from the patient data base, or both' Such systems can receive from the GUI a selected procedure; apply the selected procedure to a physiomechanical model representation of at least a portion of they, and to thereby derive a predicted effect of the selected procedure on the structure of the eye. In some embodiments the modeling system provides a representation of the predicted effect to the GUI.

In embodiments of such systems the system can include a phacoemulsification system. In embodiments of these systems, the systems are configured to perform one or more of the methods, procedures or deriving activities, set forth in this Summary of the Invention.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
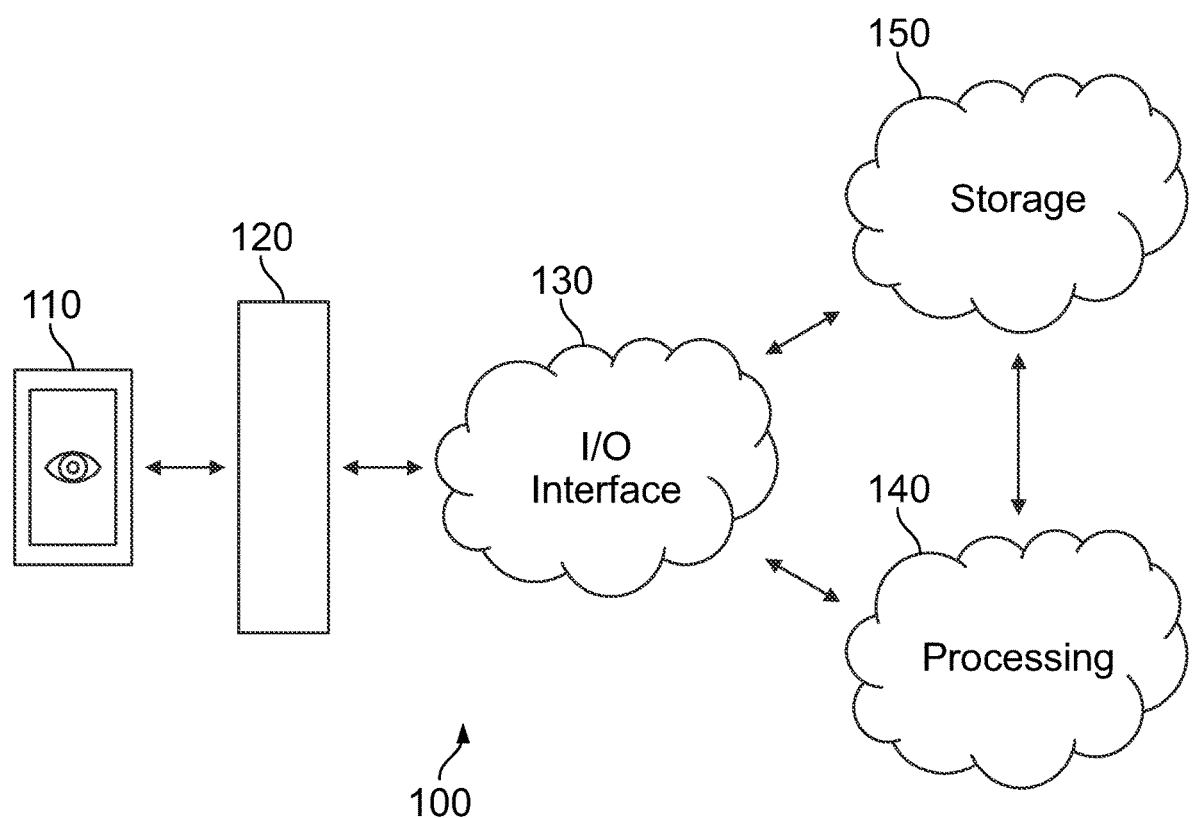
FIG. 1 schematically depicts an example of a cloud-based architecture of a system of the inventive concept.

The following description includes information that may be useful in understanding the present invention. It is not an admission that any of the information provided herein is prior art or relevant to the presently claimed invention, or that any publication specifically or implicitly referenced is prior art.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

As used herein, unless specifically stated otherwise, the terms "femtosecond laser," "femtosecond laser beam", "femtosecond pulse", and similar such terms, are used to refer to the pulse duration, and thus also pulse length of a laser beam (which can also be referred to as pulse width), and would mean all lasers and laser beams with pulse durations of less than about 10 picoseconds (less than about $10 \times 10^{-12}$ seconds) to and including about 1 femtosecond (fs) ($1 \times 10^{-15}$ seconds).

As used herein, unless stated otherwise, room temperature is about 25° C. Similarly, standard ambient temperature and pressure is about 25° C. and about 1 atmosphere. Unless expressly stated otherwise all tests, test results, physical properties, and values that are temperature dependent, pressure dependent, or both, are provided at standard ambient temperature and pressure, including viscosities.

Generally, the term "about" and the symbol "~" as used herein unless stated otherwise is meant to encompass a variance or range of ±10%, the experimental or instrument error associated with obtaining the stated value, and preferably the larger of these.

As used herein, unless specified otherwise, the recitation of ranges of values, a range, from about "x" to about "y", and similar such terms and quantifications, serve as merely shorthand methods of referring individually to separate values within the range. Thus, they include each item, feature, value, amount or quantity falling within that range. As used herein, unless specified otherwise, each and all individual points within a range are incorporated into this specification, and are a part of this specification, as if they were individually recited herein.

As used herein, unless expressly stated otherwise terms such as "at least", "greater than", also mean "not less than", i.e., such terms exclude lower values unless expressly stated otherwise.

It is noted that there is no requirement to provide or address the theory underlying the novel and groundbreaking processes, materials, performance or other beneficial features and properties that are the subject of, or associated with, embodiments of the present inventions. Nevertheless, various theories are provided in this specification to further advance the art in this area. The theories put forth in this specification, and unless expressly stated otherwise, in no way limit, restrict or narrow the scope of protection to be afforded the claimed inventions. These theories may not be required or practiced to utilize the present inventions. It is further understood that the present inventions may lead to new, and heretofore unknown theories to explain the function-features of embodiments of the methods, articles, materials, devices and system of the present inventions; and such later developed theories shall not limit the scope of protection afforded the present inventions.

The various embodiments of systems, therapies, processes, compositions, applications, and materials set forth in this specification may be used for various other fields and for various other activities, uses and embodiments. Additionally, these embodiments, for example, may be used with: existing systems, therapies, processes, compositions, applications, and materials; may be used with systems, therapies, processes, compositions, applications, and materials that may be developed in the future; and with systems, therapies, processes, compositions, applications, and materials that may be modified, in-part, based on the teachings of this specification. Further, the various embodiments and examples set forth in this specification may be used with each other, in whole or in part, and in different and various combinations. Thus, for example, the configurations provided in the various embodiments of this specification may be used with each other. For example, the components of an embodiment having A, A' and B and the components of an embodiment having A", C and D can be used with each other in various combination, e.g., A, C, D, and A. A" C and D, etc., in accordance with the teaching of this specification. The scope of protection afforded the present inventions should not be limited to a particular embodiment, example, configuration or arrangement that is set forth in a particular embodiment, example, or in an embodiment in a particular figure.

Systems and methods of the inventive concept provide a user with cloud-based interactive software that assists in ophthalmic procedures that include incision (e.g. using a femtosecond laser) and phacoemulsification of the natural lens. For purposes of this application, femtosecond lasers and/or femtosecond laser beams mean laser beams having a pulse duration of about 10 picoseconds ($10 \times 10^{-12}$ seconds) or less, about 1 picosecond ($10^{-12}$ seconds) or less, and include 1 femtosecond (fs) ($10^{-15}$ seconds). Such procedures can include insertion and placement of an artificial intraocular lens. Implementation of such systems and software can include the use of a three dimensional physiomechanical model of the eye or a portion of the eye. Such a physiomechanical model (which is described in greater detail below) can be responsive to proposed or actual modifications to the structure of the eye (e.g. incisions, lens removal, etc.) and provide representations of predicted or projected responses to such modifications to a user.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

An example of a system of the inventive concept is shown in FIG. 1. Such system (100) can include a local interface (110) that is utilized by a practitioner to input and receive information. Such a local interface can communicate via an internet interface (120), such as a website to an information network (e.g. the internet) that provides access to an input/output interface (130). Such an input/output interphase can provide communication with data storage and processing functions of the system. In preferred embodiments of the inventive concept the input/output interface (130), processing (140), and data storage (150) are cloud based, although one or more of these components or portions thereof can be embodied in system components that are local to the user. Storage components can include one or more databases utilized by processing functions of the system, and can be accessed directly by a user via the input/output interface. It should be appreciated that cloud-based storage of such databases permits updates and additions to the information stored therein to all users. Processing components of the system can incorporate one or more algorithms that receive input from a user, provide assistance in determining an optical treatment plant, generate interactive physiomechanical models of the eye and/or eye structures, etc. as detailed below. It should be appreciated that the use of cloud-based processing provides distribution of updates and improvements to all users.

Figure 2:
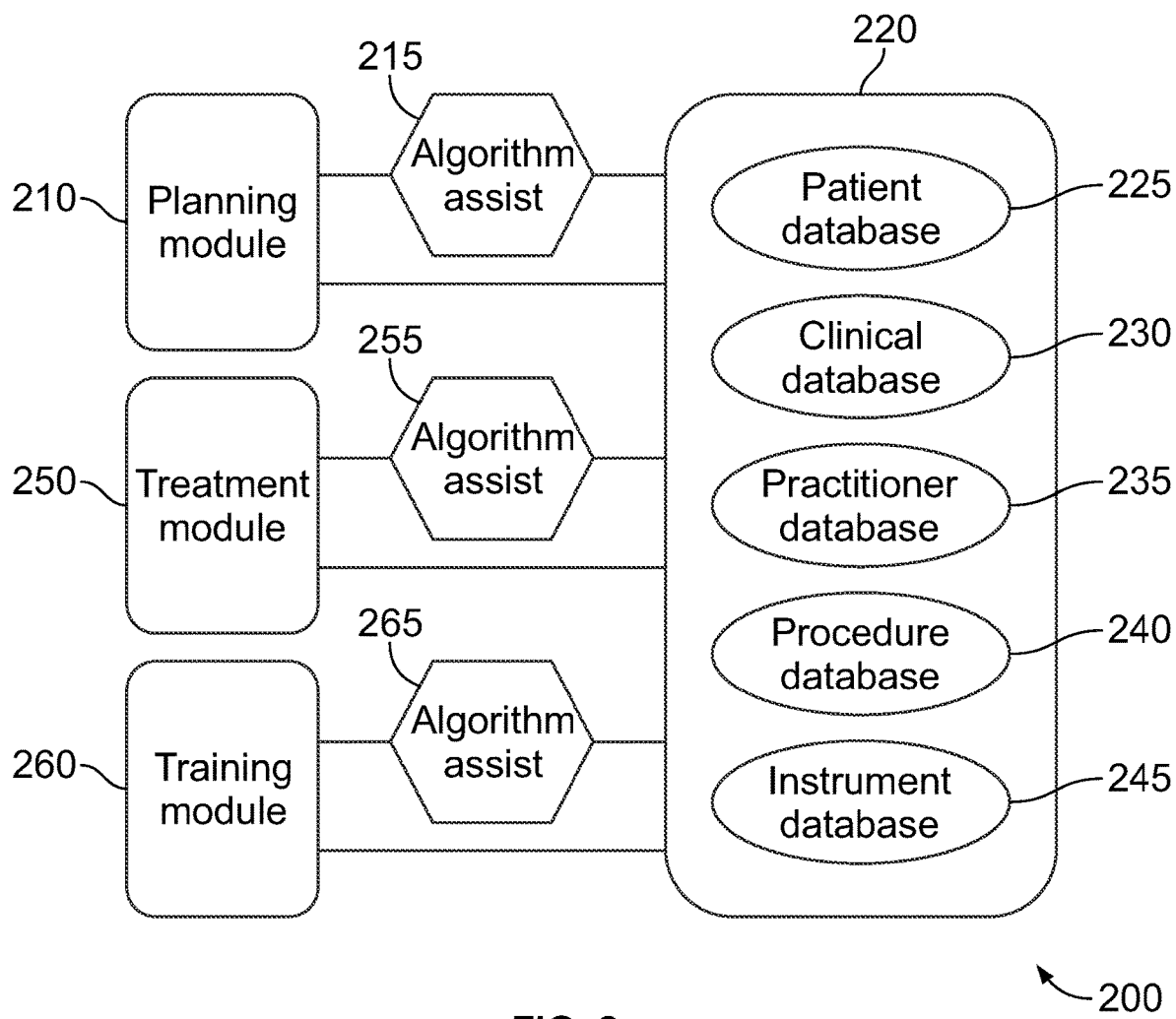
FIG. 2 schematically depicts exemplary modules of a system of the inventive concept.

An internet interface of the inventive concept can be arranged into two or more modules, as shown in FIG. 2. In the exemplary internet interface (200) shown, three different modules are provided. A planning module (210) provides a practitioner with an interface useful for planning a course of treatment. The planning module can access a database (220), either directly or through an algorithm assist (215). The database can include sub-databases that information useful to the practitioner and/or the algorithm assist. Typical sub-databases include a patent information database (225) that includes patient-specific information; a clinical database (230) that includes aggregated data related to disease states/injuries, treatment modes, outcomes, physical parameters for the eye and eye structure (e.g. for use in generating physiomechanical models), etc.; a practitioner database that includes practitioner-specific information such as specialized training/skills, experience with different treatment modes, treatment preferences, etc.; a procedure database, which can include information related to various medical intervention procedures, effects of medications, etc.; and/or an instrument database, which can include information related to the use and performance characteristics of different medical instruments, availability of instruments at different treatment facilities, etc.

In use, a practitioner can utilize a planning module to explore different treatment options and/or plan a treatment protocol for a specific patient. In some embodiments the practitioner can use the planning module to conveniently and directly access information from the database (for example, by line commands, icon-based navigation, etc.) to determine a treatment protocol based on their individual experience. In a preferred embodiment, a practitioner can utilize an algorithm assist (215) to determine an optimal treatment plan. Such an algorithm assist can include providing the practitioner with a three dimensional, interactive physiomechanical model of the eye (or a portion thereof), which can be used to input trial treatments and display the probable results. Alternatively or in addition, in some embodiments a practitioner can provide the assist algorithm with information regarding the condition or injury to be treated and the assist algorithm can apply a machine learning approach to data from the patient database and the clinical database to provide one or more suggestions for treatment plans with a high probability of success. In some embodiments the assist algorithm can utilize information from the practitioner database to adjust such suggestions to be compatible with the practitioner's skills or preferences, and can similarly utilize information from the instrument database to adjust such suggestions to utilize equipment and facilities available at the practitioner's location.

Once the practitioner is satisfied with the proposed treatment plan it can be transferred to a treatment module (250) of the internet interface, for example by storing it in the patient database (225) for retrieval. The treatment module can be used to assist a practitioner in the course of treatment, for example providing guidance during a surgical procedure. In some embodiments the treatment module can be used by a practitioner to practice a medical procedure as it would be performed, using an interactive physiomechanical model based on the patient's anatomy. In a preferred embodiment the treatment module has access to a database that is similar, identical to, or the same database (220) accessed by the planning module (210). The treatment module can provide a practitioner with direct access to information in the database, or can provide access through an algorithm assist (255). In a preferred embodiment the algorithm assist can provide a practitioner with an interactive physiomechanical model of the patient eye (or a portion thereof), which can be used to input steps of the treatment plan and to display projected outcomes of those steps. In some embodiments these can be provided as an augmented reality that is overlayed on the patient's anatomy during treatment. In some embodiments deviations from expected results can be entered during a procedure, and the system used to suggest corrective action.

The internet interface can also include a training module (260). Such a training module can be used in educating prospective practitioner, provide current practitioners with training to update or expand their skill set, and/or can be used for consultation between practitioners. In a preferred embodiment the training module has access to a database that is similar, identical to, or the same database (220) accessed by the planning module (210). The training module can utilize a stored, idealized physiomechanical model of a typical eye representing one or more disease/injury states, and to subsequently display the results of different interventions. When used for consulting purposes, one or more consulting practitioners can directly access patient-specific data and proposed treatment plans and subsequently provide feedback to the primary practitioner.

Systems and methods of the inventive concept include one or more data processing devices, one or more data storage devices, and one or more interactive algorithms. These can be implemented or accessed via a wired network, a wireless network, and/or a data and/or processing cloud system. This advantageously provides portability and a degree of device independence, permitting systems and methods of the inventive concept to be widely implemented with minimal local investment in computing hardware. Use of cloud-based data and/or processing also provides for simultaneous distribution of data and updated software, and local access to system-wide patient data. Such patient data can, in turn, be utilized by algorithms of the system to generate suggested treatment protocols and/or refine physiomechanical models. Accordingly, access to a system-wide range of patient data via a cloud-based system can improve accuracy of diagnosis and treatment of ophthalmic conditions.

Systems and methods of the inventive concept can utilize and/or incorporate a wide range of computational and display devices that can serve as a local interface. Such devices can include consumer electronic devices, including smart phones, tablet computers, wearable devices (e.g. smart watches, smart glasses), laptop computers, and desktop/tower computers. In some embodiments devices can include medical-grade electronic devices, such as binocular heads-up displays, microscope heads-up displays (e.g. for phacoemulsification procedures), and monitors/displays that are housed and configured for use in an operating theater. Such devices can provide a working image that is wholly computer generated, or can provide an augmented reality display in which computer-generated imagery is overlayed on an acquired image of an eye undergoing treatment.

Embodiments of the inventive concept include one or more databases, which can be used for storage of patient-specific data, clinical data related to ophthalmic disease, clinical data related to treatment protocols and outcomes, treatment plans, user (e.g. physician) preferences, experience of individual practitioners with different optical conditions and/or treatment methods, algorithms for selection of a treatment plan, algorithms for generation of a physiomechanical model of a patient's eye (or a portion thereof), etc. All or a part of such databases can be implemented in cloud storage, which can in turn be accessed for uploading and/or downloading via wired or wireless internet connections (e.g. via a website or similar interface).

In some embodiments of the inventive concept an algorithm can be used to assist a user (e.g. a physician) in selecting and/or optimizing an ophthalmic surgical procedure for a specific patient, based on patient specific characteristics and desired outcomes that are inputted by a user. In preferred embodiments such algorithms can be products of machine learning, and correlate patient specific characteristics and desired outcomes with stored clinical data (which can include patient data related to ophthalmic condition, age, gender, ethnicity, presence or absence of genetic markers, underlying disease, current medications, previous interventions), procedures and/or techniques applied, and observed objective and/or subjective outcomes. Other inputs include physician preferences, extent of physician experience or training with various treatment modes, and physician success rate with various procedures. All or part of such algorithms can be implemented on a cloud computing platform. Use of cloud computing advantageously permits implementation on a wide variety of platforms, as well as providing a larger and more diverse data set that facilitates accurate machine learning.

It should be appreciated that, in addition to providing an assistive algorithm for treatment optimization, systems and methods of the inventive concept can provide an interface for a practitioner (e.g. an ophthalmic surgeon) to input their individual preferences. Examples of such preferences include utilization of a particular femtosecond laser that is available in the immediate clinical setting, preferred incision depth and/or length, brand and model of intraocular lens, etc. These preferences can, for example, be inputted using a web-based checklist. In preferred embodiments the assistive algorithms incorporate these preferences into proposed treatment plans.

In some embodiments of the inventive concept a treatment plan can include more than one type of surgical intervention. For example, treatment of cataract can include use of a femtosecond laser to incise the cornea and phacoemulsification to disrupt and remove the cloudy natural lens. In such embodiments an algorithm of the inventive concept can be instructed to prioritize optimization of one surgical intervention of a procedure over another surgical intervention of the procedure. For example, in treatment of an otherwise uncomplicated cataract in a patient with significant astigmatism placement and size of a corneal incision can be used to reduce degree of post-surgical astigmatism. In such a situation the algorithm can be instructed to prioritize optimization of the femtosecond laser incision portion of the intervention over phacoemulsification. Alternatively, if a patient has a particularly problematic cataract a practitioner can choose to optimize phacoemulsification over the initial femtosecond laser incision step. Such weighting of procedure optimization can be performed by an algorithm, based on individual patient data. Alternatively, such weighting can be determined and inputted by a practitioner.

As noted above, a system of the inventive concept can include a database that records the experiences of individual practitioners in their treatment of various ophthalmic conditions and with different tools and techniques. These can be used to complement or replace clinical data input and/or results of physiomechanical modeling simulation to an algorithm for treatment optimization, thereby introducing a real-world, hands-on element to the optimization. In some embodiments a practitioner can selectively access records of the experiences of specific practitioners, and in some embodiments contact one or more selected practitioners in real time for consultation. Implementation of such features on a cloud-based system advantageously provides a large population and a consistent interface that supports effective collaboration and community interaction.

In devices and methods of the inventive subject matter patient-specific information is used to generate a dynamic and interactive three dimensional model of all or a part of one of the individual's eyes. Within the context of this description a three dimensional model is intended to encompass a two dimensional depiction provided on a computer display that provides perspective, shading, color cues, is rotatable, or includes other visual cues indicative of having length, breadth, and height. The configuration of this three dimensional model is a physiomechanical model is at least in part based on measurements of physical parameters related to the individual's eye and that are reflective of its mechanical characteristics (rigidity, elasticity, density, thickness, etc.). In some embodiments the physiomechanical model is based on a natural, unaltered eye of a patient. In other embodiments the physiomechanical model is based on an eye that has previously received medical interventions (e.g. LASIK, PRK, lens removal, artificial lens placement, vitrectomy, scleral buckle, etc.) that impact the physical, mechanical, and/or optical characteristics of the patient's eye. In such embodiments physical characteristics of modified tissue and/or artificial devices can be included as inputs to the physiomechanical model. In other embodiments, a dynamic physiomechanical model (i.e. one that shows transition from a baseline state to an altered state) can be used to show the projected effects of a medical intervention on an eye or a portion thereof can be generated using physiomechanical models of the eye derived from measurements made prior to medical intervention and the changes to those measurements that are expected from the medical intervention (i.e. pre-alteration and post-alteration, respectively).

A physiomechanical model can be dynamic and responsive to inputs from a user (e.g. a physician) that represent alterations to the subject eye. Examples of such alterations include medical interventions such as incisions made to specified portions of the eye, ablation of portions of the eye, removal or alteration of an eye structure (e.g. a lens having a cataract), addition of materials or substances to the eye (e.g. a tissue graft, an artificial lens, etc.), and administration of medications (e.g. medications that alter intraocular pressure). On receiving such inputs the physiomechanical model is modified to generate a post-alteration physiomechanical model that represents the configuration of all or a portion of the eye following the alteration inputted by the user. In some embodiments transitional physiomechanical models are derived that can provide an animatic or other dynamic display of the movements and/or configuration changes that occur during the transition between the pre-alteration and post-alteration configurations in order to facilitate understanding and interpretation of the effects of the inputted alteration. In some embodiments and overlay between the pre-alteration and post-alteration configurations can be provided to facilitate understanding and interpretation of the effects of the inputted alteration.

Figure 3:
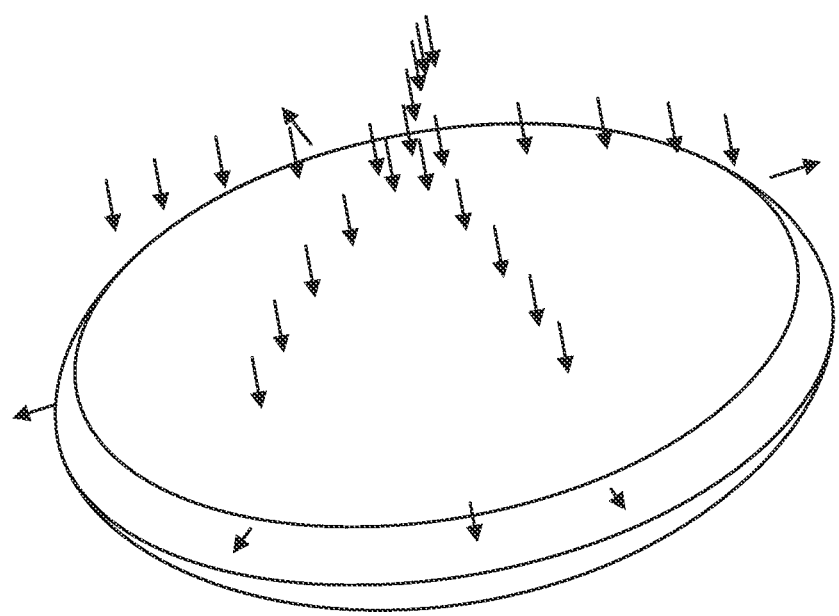
FIG. 3 is an exemplary three dimensional representation of a physiomechanical model of a lens within a capsular bag of the human eye. Shading represents the degree of mechanical strain within the structure; arrows represent the direction in which the strain is oriented.

In addition to displaying changes in shape, orientation, and/or configuration of all or part of the subject eye, the physiomechanical model can provide visual cues to provide an enhanced physiomechanical model that serves to demonstrate or highlight specific results or values for all or part of the model. For example, color coding can be used to emphasize characteristics of surface topography (for example, of the cornea following ablation) and/or mechanical strain that may not be readily observable in an unenhanced physiomechanical model. FIG. 3 provides an exemplary three dimensional representation of a physiomechanical model of a lens within a capsular bag of the human eye. Shading represents the degree of mechanical strain within the structure; arrows represent the direction in which the strain is oriented. Similarly, ray tracing indicating the refraction of one or more wavelengths of light passing through structures of the eye can be used to indicate where best focus occurs in order to evaluate the effects of implantation of an artificial lens. In some embodiments such enhancements can be combined, for example to evaluate the effect of laser ablation to correct corneal defects in an eye that is receiving an artificial lens.

Physiomechanical models of the inventive concept can be used by a practitioner to evaluate the outcomes of different interventions and/or procedures on a patient's eye in order to develop a treatment plan that best addresses their individual condition. As such it provides a tool that leverages the practitioner's training and experience in combination with a virtual model reflecting results of inputted interventions on a specific eye, permitting the practitioner to develop an effective treatment plan using techniques and tools at their disposal and with which they have the greatest degree of familiarity and comfort. Such an interactive physiomechanical model can also be used to develop treatment plans that utilize combinations of familiar treatment modes (e.g. ablation, lens replacement, and medication) that otherwise would otherwise not be considered.

In some embodiments an initial physiomechanical model can be utilized to determine an optimal procedure that acts as a step in a multi-step procedure (for example, an incision into the cornea using a femtosecond laser as an initial step in lens removal). This can be followed by use of a second physiomechanical model reflecting changes in the mechanical properties of the eye or a portion of the eye (e.g. as a result of the initial procedure) to determine an optimal procedure for a subsequent step (e.g. phacoemulsification, intraocular lens placement, etc.). In some embodiments the second physiomechanical model is based on projected mechanical characteristics derived from the calculated effects of the first procedure on the initial physiomechanical model. In other embodiments mechanical properties of the eye or eye structure determined by measurements taken following the initial procedure are used to derive such a second physiomechanical model.

Figure 4:
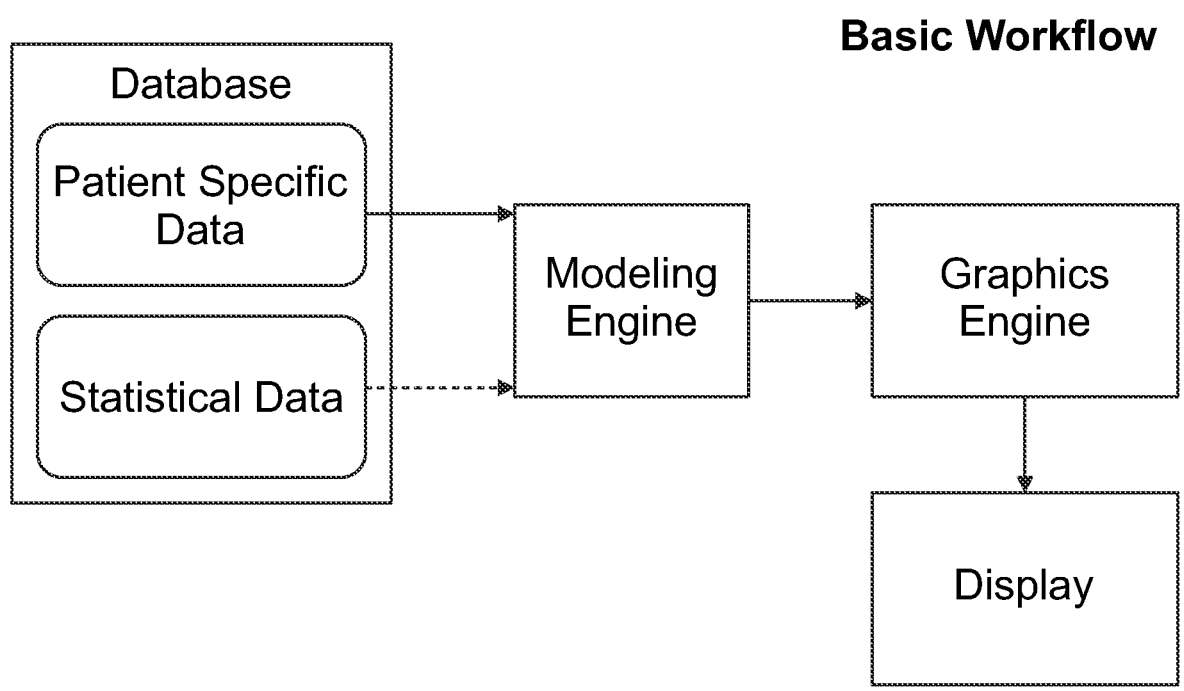
FIG. 4 provides a flowchart of a general workflow in a system of the inventive concept.

An example of a general workflow for a system of the inventive concept is shown in FIG. 4. As shown, such a system can include a database, which in turn can store patient specific data derived from measurements made of the patient's eye, patient history, etc. as detailed below. Such a database can also include statistical data derived from population studies, which can include recorded outcomes of specific interventions and/or procedures as well as characteristics of specific sub-populations. Information from the patient specific database (and in some implementations the statistical database) is provided to a modeling engine. The modeling engine utilizes this data to generate a patient-specific in numero physiomechanical model of the eye or a portion thereof based on the patient specific data. For example, the modeling engine can apply basic mechanical principles to measurements and known properties of a portion of the eye to extrapolate properties such as curvature, surface topography, probability of loss of integrity, etc. Alternatively, the modeling engine can apply patient specific data along with calculated and/or known properties of structures of the eye to calculate a strain energy for the eye or portions thereof, then iteratively apply different configurations and/or dimensions (within allowable limits) to generate a low-strain energy configuration. In some embodiments such approaches can be combined. In some embodiments such calculated in numero models can be compared to information derived from the statistical data, and/or modified using same.

Such an in numero model provided by the modeling engine can be supplied as representational data to a graphics engine, which serves to provide a human-perceivable output to a display. In a preferred embodiment this is in the form of an output suitable for a three dimensional display or a functional two dimensional representation of a three dimensional model. Other display formats are also considered, including tabular outputs, written or verbal recommendations, graphical or color-keyed indications of the probability of desired outcome, etc.

Figure 5:
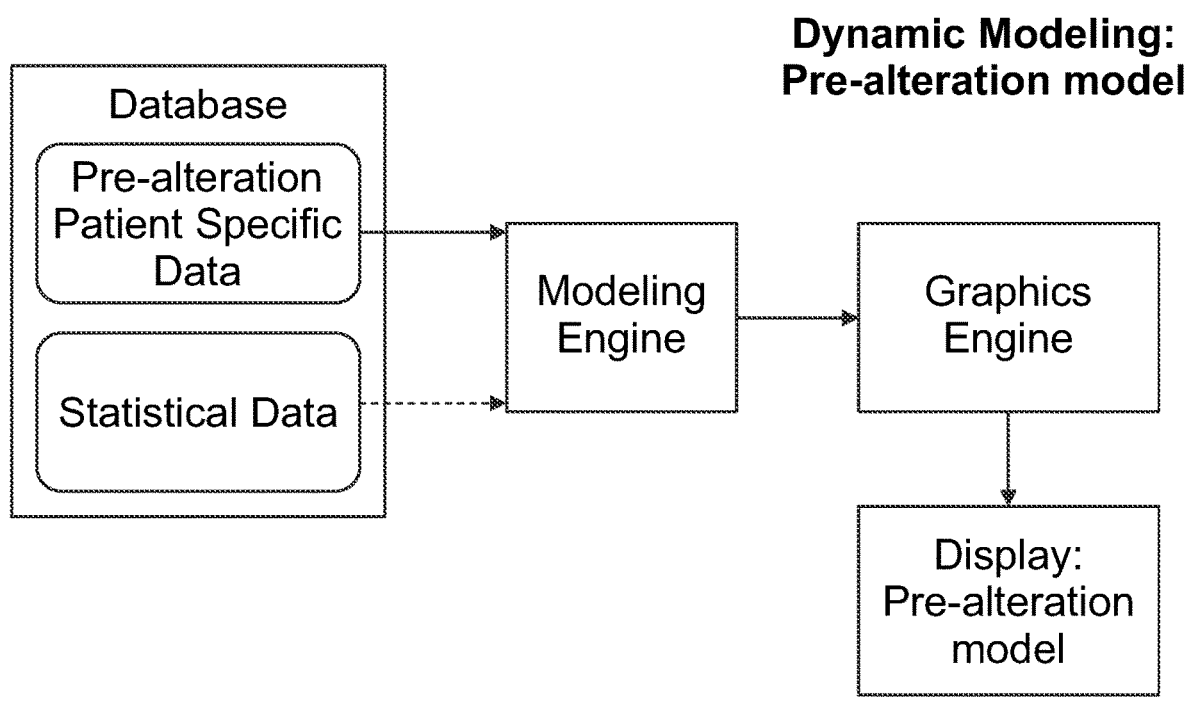
FIG. 5 provides a flowchart of a workflow in a system of the inventive concept to generate a pre-alteration physiomechanical model.
Figure 6:
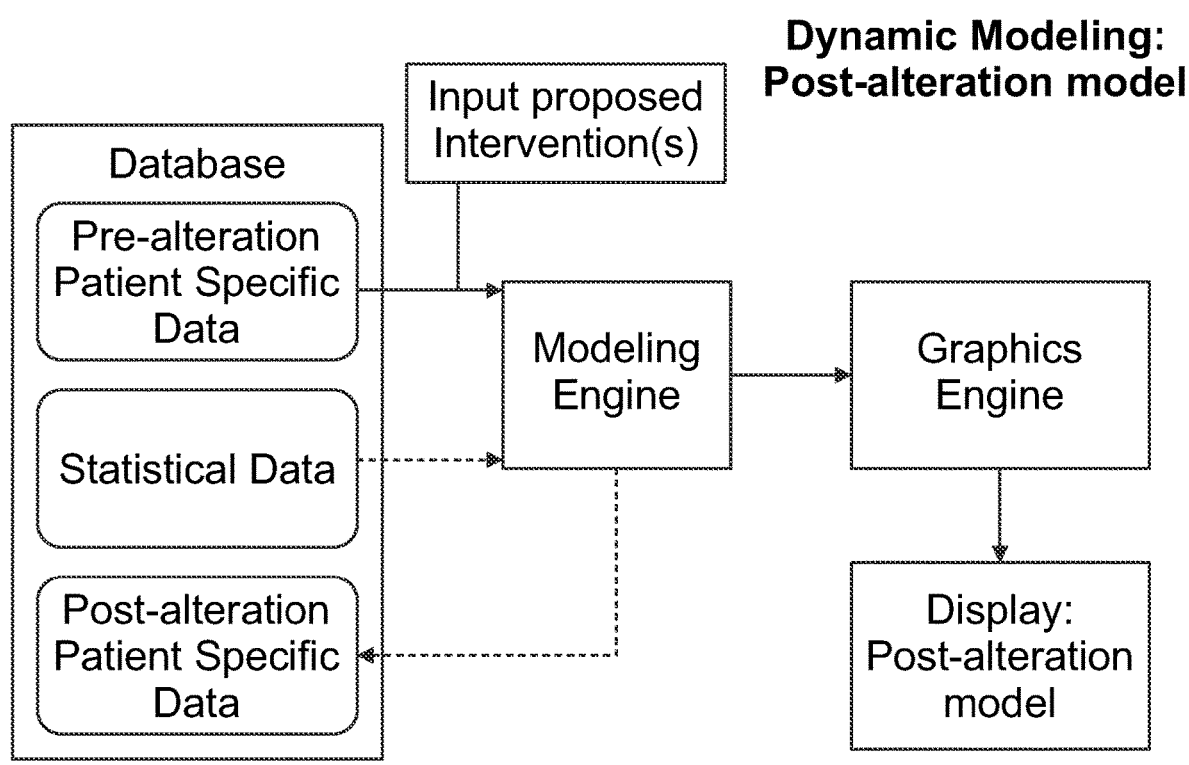
FIG. 6 provides a flowchart of a workflow in a system of the inventive concept to generate a post-alteration physiomechanical model.

As shown in FIG. 5, in some embodiments an initial pre-alteration in numero model of a specific patient's eye or portion thereof can be generated using patient-specific data derived from measurements, history, etc. to a modeling engine. This in turn provides representational data descriptive of the patient's eye prior to intervention to the graphics engine, which can provide input to a display that can in turn provide a human-observable representation of the patient's eye or a portion thereof prior to medical intervention. This can serve as a baseline or starting point for a dynamic physiomechanical model that provides "before and after" views of the effects of a proposed medical procedure. Similarly, FIG. 6 shows a workflow of a similar process in which the graphics can provide input to a display that can in turn provide a human-observable representation of the patient's eye (or a portion thereof) following a medical intervention. This can serve as an endpoint of a proposed medical procedure or, alternatively, as a midpoint result of complex/multistep medical procedure.

Figure 8:
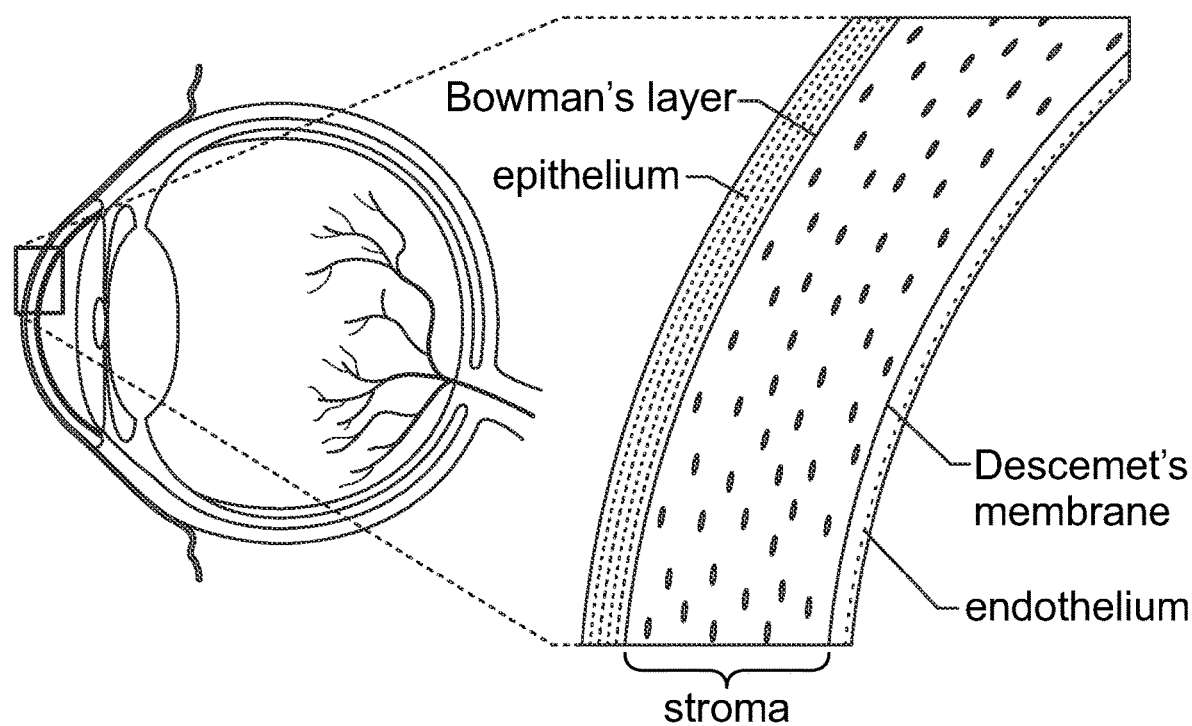
FIG. 8 provides a cross sectional view of the cornea and associated structures.

As shown in FIG. 8, in some embodiments a post-alteration in numero model of specific patients eye or a portion thereof can be generated by inputting one or more proposed interventions, which alter the values of the patient specific data. In some embodiments the impact of such interventions on the pre-alteration specific data is determined by the modeling engine, which in turn utilizes these revised values to derive a post-alteration in numero model. In other embodiments revision of the values of the pre-alteration specific data is carried out in a separate operation that generates a post-alteration patient specific dataset in the database. This post-alteration patient specific dataset can then be accessed by the modeling engine and used to generate a post-alteration in numero model. As with generation of a pre-alteration in numero model, data from the statistical dataset can be used to determine optimal model generation methodology and/or to modify a post-alteration in numero model based on group historical data. Once the post-alteration in numero model is determined a set of post-alteration representative data that is provided to the graphics engine, which in turn provides a human-observable output (for example, via a display) that represents the post-alteration outcome of the proposed intervention.

In some embodiments, post-alteration specific data derived from an in numero model can be entered into the database. Such post-alteration specific data can then be used as an origination point for calculating the effects of a subsequent proposed intervention, which in turn generates a second post-alteration physiomechanical model. Such a sequential approach can be used to derive an optimal treatment plan for a complex procedure that includes a number of distinct steps. For example, an initial post-alteration model can be used to determine optimal size and placement for a corneal incision and a subsequent post-alteration model can be used to determine optimal intraocular lens selection and placement in treatment of cataract.

Generation of a physiomechanical model can include inputting patient specific data, including various physical characteristics of the individual eye to be treated into a specified patient specific database. Such data can include corneal acoustic response and/or ultrasound data, topographic data, pachymetric data, elevation data, corneal thickness data, corneal curvature data, wave front data, intraocular pressure data, peripheral stromal thickness data, patient age, patient gender, duration of contact lens use, prior surgical intervention, and/or response to prior surgical intervention. Such data can be acquired corneal topography, optical coherence tomography, wave front analysis, ultrasound, and/or patient interview.

Data gathered in this manner can be used to determine or infer a variety of mechanical properties that can be used to derive a physiomechanical model of the eye or an eye structure. Such mechanical properties include Young's modulus, stress/strain modulus of elasticity, Poisson's ratio, density, hardness, ductility, and/or results of finite element analysis of eye structures under compression, tension, torsion, shear. It should be appreciated that these can be modified by temperature, which can be varied to some extent during a procedure.

Such patient-specific data can be acquired and entered for any relevant eye structure. Relevant eye structures include the lens, capsular bag, zonule sclera, cornea, iris, epithelium, ciliary and muscle, anterior chamber with aqueous humor, posterior chamber with vitreous humor, suspensory ligaments, pupil, canal of Schlem, trabecular meshwork, conjunctiva, corneal limbus, and/or retina.

Embodiments of the inventive concept can also include a statistical database that includes data derived from a population of patients that have undergone ophthalmic treatment. Such a statistical database can include data related to specified population segments (e.g. age range, gender, ethnicity, presence or absence of specified genetic markers), ophthalmic conditions, applied interventions/treatments, and outcomes. Such a statistical database can also include information related to correlations between characteristics of a specified population segment, interventions and/or treatments applied, and outcomes. In some embodiments such data and/or correlations can be accessed to aid in deriving characteristics of a post-alteration physiomechanical model. Use of such a statistical database can improve accuracy of such a post-alteration physiomechanical model by providing statistically sound estimates for values not provided in a patient-specific database. For example, patient specific factors such as age, gender, and past treatment can be used to define a population segment within the statistical database that can provide statistically sound estimates of patient-specific values that are not present in the patient-specific database.

Changes in shape associated with interventions directed to one or more portions of the eye can be calculated using one or more mechanical model(s) that provide estimates of curvature, etc. based on mechanical characteristics of structures of the eye. Such mechanical characteristics can be derived from individual data stored in the database, and recalculated following alteration of those characteristics by medical intervention. Examples of such mechanical characteristics include Young's modulus (E), which provides a measure of elasticity of structure, and Poisson's ratio, which is the ratio of lateral contraction strain to longitudinal extension strain in the direction of a stretching force. These can be estimated from appropriate measurements. For example, $(1-v2)P\cdot-(1)E=2\ aK(a/h,v)w$, where:

E is Young's modulus
P is the indentation force
v is Poisson's ratio
w is the indentation depth
a is the radius of the indentor
h is the thickness of the tissue
K is a scaling factor that depends on the aspect ratio a/h Poisson's ratio A solution can be obtained based on the assumption of an infinitesimal deformation of indentation. Alteration of components of the eye can alter parameters that impact mechanical characteristics (such as Young's modulus) of such components. For example, modification of the thickness of a portion of the cornea by laser ablation directly impacts tissue thickness in that region. The modeling engine can be used to estimate the effect of eye structure parameters altered by proposed medical intervention on such mechanical characteristics, and apply forces within the eye (such as intraocular pressure) to project the impact on the configuration of such structures in order to generate a physiomechanical model of the post-alteration eye. Similarly, the effect of such changes in configuration in a specific eye structure on adjoining or otherwise coupled eye structures can be calculated and utilized in post-alteration physiomechanical model. Pre- and post-alteration physiomechanical models of an individual eye or portions thereof can be combined to generate a dynamic physiomechanical model of the eye based on mechanical estimation.

Alternatively, an energy minimization approach can be utilized in which values from the patient-specific database are provided to a modeling engine that generates a mathematical model of the relationship between forces present within the eye or portion of the eye and characteristics of the eye or portion of the eye, as derived from mechanical relationships as described above. This mathematical model provides a set of coordinates used in generating the three dimensional physiomechanical model, which can represent a low or minimized energy solution to the mathematical model. In some embodiments this mathematical model is applied to the eye or a specified portion of the eye as a whole. In other embodiments a series of mathematical models are applied to segments of the eye or specified portion of the eye to generate a mathematical model set, where each member of the set provides a correlation between forces present within its respective segment and the characteristics of that segment. In such an embodiment an additional integrating model is be derived that characterizes the interactions between such segments.

The modeling engine can further output one or more sets of representational data used to derive coordinates for representation of a physiomechanical model, based on established mechanical relationships between stored physical parameters (e.g. density, thickness, elasticity, rigidity, etc.) and applied and/or inherent forces present in the eye. Such mechanical relationships can be applied to generate representational data that represents a set of coordinates that provides a lowest static energy solution for the physiomechanical model as determined by calculation of strains and stresses within the structure.

For example, well known mechanical relationships can be used to derive a baseline strain or static energy resulting from application of stored physical parameters (which can be the results of measurements from an individual) to a stored baseline or generic physiomechanical model that includes a set of baseline spatial coordinates of generic eye or a desired portion of the eye. The modeling engine then applies a static energy reduction algorithm to modify spatial coordinates of this modified baseline physiomechanical model to reduce or minimize the baseline static energy. Such an algorithm can, for example, calculate strain or static energy for a variety of possible dimensions as limited by known characteristics of the eye or eye structure in an iterative fashion, then ranking the results. The final physiomechanical model is realized when this static energy is minimized (i.e. further modification results in increased calculated static energy or strain).

In another embodiment of the inventive concept, the eye or a portion thereof (e.g. the cornea) can be modeled as a flexible laminated structure. Such a lamellar model can include two or more layers that are attached to each other, such that a surface of one of the layers is in contact with and continuously adhered to a corresponding surface of an adjacent layer. In doing so a lamellar physiomechanical model can be more completely representative of actual eye and/or eye structure within naturally occurring anatomical context than strictly mechanical and/or energetic approaches. In such a lamellar model adjacent layers can have difference thicknesses, compositions, and mechanical properties, and can be selected and ordered to at least partially replicate anatomy of the eye and its different tissue layers. Such a lamellar physiomechanical model can, for example, provide for a relatively thin and flexible epithelial layer adhered to an inflexible Bowman's layer, which is in turn adhered to a relatively thick and flexible stroma of varying density in a physiomechanical model of the cornea, and account for modification of any or all of these layers.

Figure 9:
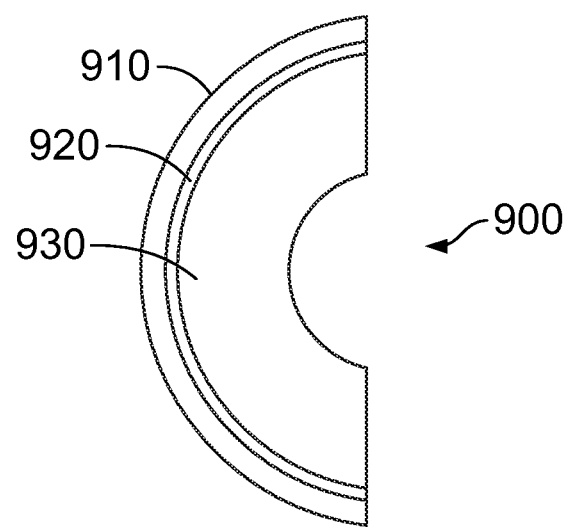
FIG. 9 provides a schematic depiction of a lamellar model of a portion of the eye, as in the inventive concept.

An example of such a lamellar model is shown in FIG. 9, which depicts an exemplary lamellar model of a portion of a cornea. The lamellar model (900) incorporates three layers (910, 920, 930), which are modeled as having individual mechanical/physical characteristics corresponding to the epithelial layer (910). Bowman's layer (920), and stroma (930). The lamellar physiomechanical model (900) is generated by treating the overall structure as a flexible laminate in which layer (910) is continuously adherent to layer (920), and layer (920) is continuously adherent to layer (930).

Basic mechanical properties for various portions of the cornea are available (see Masterson and Ahearne, Experimental Eye Research, 177:122-129 (2018); Last et al., Journal of Structural Biology, 167(1):19-24 (2009)), and can be further refined based on patient-specific data (e.g. measurements, age, medical history, etc.). A physiomechanical model based on the resulting lamellar model of the eye or a portion thereof, its responses to stress (e.g. intraocular pressure), its responses to alterations in thickness (e.g. by photoablation) or stiffness (e.g. by crosslinking) of all or a portion of one or more layers, etc. can be generated in numero by any suitable method. For example, artificial neural networks trained using previously recorded data can be used to generate a predictive physiomechanical model of a lamellar structure. Multi-continuum theory has been applied to predict the behavior of flexible laminated composites, and can be applied in a similar fashion to generate a lamellar physiomechanical model. Tools such as the ANSYS Workbench™ have been used to provide three dimensional CAD models of synthetic layered composites, and can be applied to generate a lamellar physiomechanical model.

In some embodiments of the inventive concept, a model of a portion of the eye can be generated by a first method, and the resulting portion incorporated into a larger structure that is modeled by a second method. For example, if an energy minimization approach is found to provide adequate results for a portion of the cornea a first model representing such a portion can be generated in that manner. Once generated such a first model could be incorporated as a layer within a more complex lamellar model of the cornea that incorporates further layers with distinct mechanical properties. Such a combined approach can advantageously reduce computational burden.

In some embodiments the modeling engine can provide results derived in a single operation. In other embodiments a series of trial solutions can be applied iteratively until a low static energy, suitable mechanical estimation, or suitable lamellar model solution is identified. When a single mathematical model is derived for an eye or a portion thereof a single set of representational data can be used. For example, if it is desired to only model the lens of an individual's eye a single mathematical model can be adequate to describe the relationship between forces applied to portions of the lens and the physical characteristics of that lens, which in turn defines the shape of the lens as expressed as the representational data.

Alternatively, if a physiomechanical model of more extensive or complex structures is desired a mathematical model set directed to segments or portions of the desired structure or structures can be used to derive coordinates for each of the designated segments or portions that represent the designated eye or eye portion. Accordingly, known mechanical relationships can be applied to patient-specific data related to a segment as applied to a corresponding baseline physiomechanical model segment of a generic eye or eye portion to derive a baseline static energy value for that segment. An integrated static energy for the overall eye or portion thereof by applying spatial coordinates from the static energy-minimized physiomechanical models of each segment to an integrating model that defines the spatial relationships between individual segments. Spatial coordinates of individual segments can then be adjusted in an iterative manner to generate an integrated physiomechanical model with minimized static energy. In some embodiments it is desirable to only partially minimize static energy of each segment prior to minimizing static energy of the integrated physiomechanical model.

In some embodiments of the inventive concept the results of a mechanical estimation model, energy minimization, and/or lamellar model can be combined to provide a blended physiomechanical model of the eye. In such a combined approach weighting can be applied to results from mechanical estimation, energy minimization, and/or lamellar models to adjust the relative contribution of each to the final physiomechanical model. In some embodiments results of pre- and post-alteration mechanical estimation physiomechanical models and energy minimization physiomechanical models can be compared to data from the statistical database derived from patients with similar characteristics to that of the specific patient and procedures that correspond to the proposed medical intervention. If such a comparison shows that one of the mechanical estimation approach, the energy minimization approach, a lamellar model, or a combined approach is in closer agreement with data from the statistical database than the individual models, than the physiomechanical modeling approach that provides the best match can be preferentially utilized in emulations and treatment plans for the specific patient.

In some embodiments of the inventive concept a static energy-minimized physiomechanical model, mechanical estimation model, and/or lamellar model of the eye or eye portion can be further modified by data from the statistical database. Such modification can provide a more accurate outcome in instances where the patient's eye is incompletely characterized prior to generation of the physiomechanical model and/or in instances where the phenomena is recorded but understanding of underlying mechanisms is incomplete. For example, if the statistical database includes data indicating that use of a particular configuration of corneal ring is associated with greater than expected flattening of the corneal surface in a specific patient population to which the patient belongs, the spatial coordinates used to generate the three dimensional physiomechanical model of the corneal surface can be adjusted to reflect this.

As noted above, an output of the modeling engine can be a set of spatial coordinates representing the configuration of the three dimensional physiomechanical model. Such spatial coordinates are provided to a graphics engine, which in turn generates the three dimensional representation. A dynamic physiomechanical model showing projected results of a proposed medical intervention from a baseline condition can be displayed as a dynamic or animated three dimensional representation based on appropriate sets of such spatial coordinates. Such a three dimensional representation can be displayed as a surface or set of surfaces, a three dimensional surface with a portion removed to reveal internal structures, a partially translucent or transparent structure, and/or a cross section. Similarly, while a solution for the whole eye or desired portion of the eye is derived the modeling engine can be used to generate a three dimensional representation of a portion of the whole. For example, while a physiomechanical model of an entire eye is generated a user may wish to only display a portion of the physiomechanical model representing the lens or the corneal surface. Nevertheless, characteristics of this displayed portion are derived from calculations performed on data related to the entire eye or portion thereof.

The graphics engine can provide output for any suitable display. As noted above, within the context of this description a three dimensional display can include an image displaying perspective, shading, color cues, ability to be rotated, etc. indicative of three dimensional nature using a conventional two dimensional computer display. Alternatively, the graphics engine can provide output for a holographic, binocular display, virtual reality set, or other three dimensional display technology. In some embodiments of the inventive concept outputs of the graphics engine can be incorporated into an enhanced reality system in combination with images of the patient's eye. In some embodiments the graphics engine can provide output to a three dimensional printer in order to produce physical representation of projected results of treatment. Such physical representations can include differences in color, density, and/or pliability in order to represent the characteristics of the tissues of the eye or portion thereof so represented. Such three dimensional representations can have particular value as an aid in preparing for ophthalmic surgery and/or educational aids for both patients undergoing treatment and practitioners.

In some embodiments a graphics engine is not used to provide graphical feedback to a user. In such embodiments feedback can be provided in the form of a tabular representation of results or a written summary of potential positive and/or negative outcomes. In some embodiments such summaries can include recommendations for alternative procedures. In still other embodiments feedback can be provided to a user in a non-representative visual form, for example providing color-encoded icon or display indicative of positive or negative results.

As noted above, physiomechanical models of the inventive concept can be used in an interactive system that permits a medical practitioner to determine the results of various medical interventions in the diseased or abnormal eye of an individual. Towards that end an emulation system that incorporates the physiomechanical modeling system described above can include mechanisms for inputting data related to the planned intervention. Such data can be obtained from a treatment database that includes data related to specified interventions, such as laser ablation patterns, PRK incision patterns, known phacoemulsification processes, specified models of intraocular lenses, etc. Such information can be selected by a user and applied to a pre-alteration physiomechanical model of an eye to generate a post-alteration physiomechanical model. Such pre- and post-alteration physiomechanical models can be combined to generate a dynamic physiomechanical model that shows the effects of one or a series of proposed medical procedures performed on the eye. Such a dynamic physiomechanical model can be used in emulation for designing or planning a treatment method for the individual patient with a high expectation of success relative to relying only on an individual physician's training and experience.

In some embodiments data relating to the planned intervention can be entered by the user in a dynamic fashion through user selection of an appropriate intervention tool and application to the pre-alteration physiomechanical model via an appropriate interface. For example, in some embodiments a user can use a mouse or similar pointing device to draw a pattern for LASIK ablation or PRK incision on the cornea of a pre-alteration physiomechanical model of a patient's eye displayed on a computer screen and then input specified ablation parameters or incision depths prior to generation of the post-alteration physiomechanical model. Alternatively, a user wearing a VR set can use a sensor glove or similar device to virtually select and manipulate a virtual tool within a virtual environment that includes a physiomechanical model of the pre-alteration eye. In some embodiments the sensor glove can include haptic feedback or other tactile feedback devices in order to more closely emulate physical reality. In such embodiments a series of post-alteration physiomechanical models can be derived and displayed as the proposed intervention is applied in order to provide an at least approximately real-time emulation of the effects of the intervention of the eye. This advantageously allows for correction within the emulated procedure, which in turn can lead to the development of more efficient and effective intervention procedures.

Methods for generating physiomechanical models of the eye and the effects of medical procedures on the eye of a specific patient can be implemented as part of a treatment system. Such a treatment system can include memory for storage and retrieval of database information as described above, a user interface, and a display. Throughout the following discussion, numerous references will be made regarding servers, services, interfaces, portals, platforms, or other systems formed from computing devices. It should be appreciated that such computing devices are considered as having at least one processor configured to execute software instructions stored on a computer readable tangible, non-transitory medium. For example, such systems can be implemented on a server can include one or more computers operating as a web server, database server, or other type of computer server in a manner to fulfill described roles, responsibilities, or functions. Alternatively, such systems can be realized as standalone devices. In some embodiments, such treatment systems can be in communication with or coupled to devices used in treatment of the eye (e.g. a LASIK system), and can be used to provide guidance during a procedure.

EXAMPLES

Figure 7:
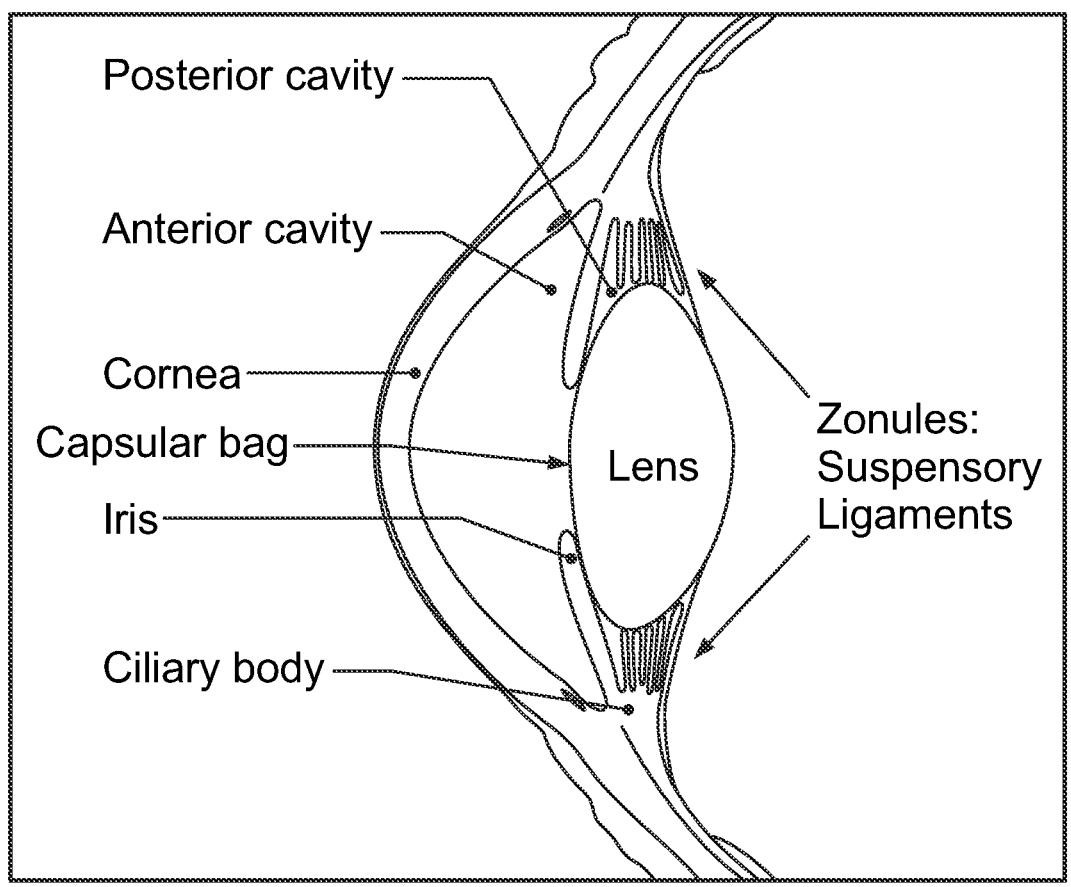
FIG. 7 provides a cross sectional view of the human eye.

In an example of generation of a physiomechanical model of a portion of the eye and the use thereof, a practitioner wishes to open the capsular bag surrounding the lens of a specific patient without causing sufficient damage to hinder subsequent positioning of an intraocular lens. A representation of a cross section of the eye is provided in FIG. 7. As shown, the capsular bag enclosing the lens is surrounded by and connected to various structures of the eye that can impact its shape and position.

Physiomechanical data related to various parts of the eye can be derived from measurements of an individual patients eye such as intraocular pressure, density, wavefront scans, etc., or modifications that individualize statistical data can be made using such measurements. Such data can be represented, for example, using look up tables, which can in turn be stored in a patient-specific database. This information can be used to generate a physiomechanical model of a patient's pre-alteration eye or eye structure. Similarly, changes made to such values as a result of medical intervention can be provided in similar tables and subsequently used to generate a physiomechanical model of a post-alteration eye or eye structure. Such models can be combined to form a dynamic physiomechanical model of the patient's eye or eye structure.

An example of a typical look up table directed to physiomechanical characteristics of an individual patient's lens is as follows:

| Patient Eye Scan Data | Population Mean | Individual's Lens value |
|---|---|---|
| a. p = Density (Scheimpflug ™ lens densitometer; Oculus Pentacam ™) | | |
| i. Perimeter | 1.070 gm/cm³ | 1.087 gm/cm³ |
| ii. Center | 1.056 gm/cm³ | 1.081 gm/cm³ |
| iii. Surface | 1.072 gm/cm³ | 1.090 gm/cm³ |
| b. Diameters (Scheimpflug ™ lens densitometer; Oculus Pentacam ™) | | |
| c. Diameter-transverse | 9.5 mm | 9.58 mm |
| Astigmatism variation | 0% mm | 0.1% mm |
| d. Diameter-sagittal | 9.5 mm | 8.380 mm |
| Astigmatism variation | 0% mm | 20% mm |
| e. Thickness [axial length] | 4.000 mm | 4.178 mm |
| ((Scheimpflug ™ lens densitometer; Oculus Pentacam ™)) | | |
| f. Anterior IOP (Applamatton ™ tonometer; air puff) | 16 mm/hg | 20 mm/hg |
| g. Surface shape data (Optical Coherence Tomography, X-sectional and 3D images) Itrace ™ aberrometer/topographer, StratusOCT ™ instrument model 3000 (Carl Zeiss Meditec), ultrasound pachymeter, transverse, saggital or axial lengths, perimeter, center from ultrasound) | CAD model | Actual vectors |
| h. Surface hardness (Shore) (computed, based upon OCT pixel unit density) | SD48 | SD50 |

An example of a typical look up table directed to physiomechanical characteristics of an individual patient's capsular bag is as follows:

| Patient Eye Scan Data | Mean | Individual's capsular bag value |
|---|---|---|
| a. p = Density (Scheimpflug ™ lens densitometer; Oculus Pentacam ™) | | |
| i. Perimeter | 1.125 gm/cm³ | 1.100 gm/cm³ |
| ii. Center top | 1.100 gm/cm³ | 1.001 gm/cm³ |
| iii. Center bottom | 1.172 gm/cm³ | 1.190 gm/cm³ |
| b. Diameters (Scheimpflug ™ lens densitometer; Oculus Pentacam ™) | | |
| c. Diameter-transverse ellipse | 10.1 mm | 10.2 mm |
| Astigmatism variation | 0% mm | 0.2% mm |
| d. Diameter-sagittal ellipse | 9.3 mm | 8.780 mm |
| Astigmatism variation | 0% mm | 10% mm |
| e. Thickness of wall | 6.2 um | 5.2 um |
| ((Scheimpflug ™ lens densitometer; Oculus Pentacam ™) | | |
| f. Anterior IOP (Applamatton ™ tonometer; air puff) | 16 mm/hg | 20 mm/hg |
| g. Shape (Optical Coherence Tomography, X-sectional and 3D images, Itrace ™ aberrometer/topographer, StratusOCT ™ instrument model 3000 (Carl Zeiss Meditec), ultrasound pachymeter, transverse, saggital or axial lengths, perimeter, center from ultrasound) | CAD model | Actual vectors |

An example of a typical look up table directed to physiomechanical characteristics of an individual patient's zonules is as follows:

| Patient Eye Scan Data | Mean | Individual's Zonule value |
|---|---|---|
| a. p = Density @ (Scheimpflug ™ lens densitometer; Oculus Pentacam ™) | | |
| Inner | 0.910 gm/cm³ | 0.887 gm/cm³ |
| Outer Perimeter | 1.000 gm/cm³ | 1.20 gm/cm³ |
| b. Diameters (Scheimpflug ™ lens densitometer; Oculus Pentacam ™, Ultrasound Biomicroscopy) | | |
| Diameter-transverse | 10.5 mm | 9.68 mm |
| Astigmatism variation | 0% mm | 0.1% mm |
| Diameter-sagittal | 11.5 mm | 11.380 mm |
| Astigmatism variation | 0% mm | 20% mm |
| c. Thickness | 0.240 mm | 0.211 mm |
| (Scheimpflug ™ lens densitometer; Oculus Pentacam ™) | | |
| d. Anterior IOP (Applamatton ™ tonometer; air puff) | 16 mm/hg | 20 mm/hg |
| e. Surface shape (Optical Coherence Tomography, X-sectional and 3D images, Itrace ™ aberrometer/topographer, StratusOCT instrument model 3000 (Carl Zeiss Meditec), ultrasound pachymeter, transverse, saggital or axial lengths, perimeter, center from ultrasound) | CAD model | Actual vectors |
| f. Surface hardness (Shore) (computed, based upon OCT pixel unit density) | SD48 | SD50 |

As noted above, known mechanical principles are applied to such patient specific values in order to generate a predictive three dimensional physiomechanical model using known mechanical principles. For example, Young's modulus for stress and/or strain can be extrapolated for various eye structures based on recorded patient specific values. Suitable eye structures include the lens, capsular bag, zonule sclera, cornea, iris, epithelium, ciliary and associated muscle, anterior chamber with aqueous humor, posterior chamber with vitreous humor, suspensory ligaments, pupil, Canal of Schlem, trabecular meshwork, conjunctiva, corneal limbus, and retina.

Applications of methods and devices of the inventive concept are widespread. Examples include use of a physiomechanical model in optimizing results of LASIK in order to determine the pattern and depth of corneal ablation prior to cutting the corneal flap. This is particularly true when native properties of the cornea have been altered, for example by crosslinking (which increases stiffness) and/or prior LASIK or PRK procedures. Physiomechanical models of the eye can also be applied to procedures in which incisions traditional made using blades are made by femtosecond lasers, which produce much narrower incisions than blades and result in different mechanical properties for the incised structure. Physiomechanical models of an individual's cornea can be used to evaluate the results of different RF intensities, durations, and targeting in Conductive Keratoplasty® procedures that modify corneal stiffness, and improve the results of monovision correction of presbyopia. Physiomechanical models of an individual's cornea and lens can be used to optimize waveform, time, intensity, and incision placement for phacoemulsification. Similarly, physiomechanical models of an individual's eye can be used to optimize artificial lens selection and placement for optimal vision results, particularly where the patient has had previous LASIK or PRK modification of the cornea and/or has extreme myopia or hyperopia that alters the configuration of the globe.

In another embodiment of the inventive concept, a modeling engine is in communication with a femtosecond laser system for preforming procedures on the lens and/or cornea (including those relating to cataract removal/replacement) and refractive procedures (such as limbus relaxing incisions, and micro-incisions in the cornea). Femtosecond lasers, and femtosecond laser beams, as those terms are used herein, refer to all lasers and laser beams with pulse durations of less than about 10 picoseconds (less than about $10 \times 10^{-12}$ seconds) to and including about 1 femtosecond (fs) (about $1 \times 10^{-15}$ seconds).

Figure 10:
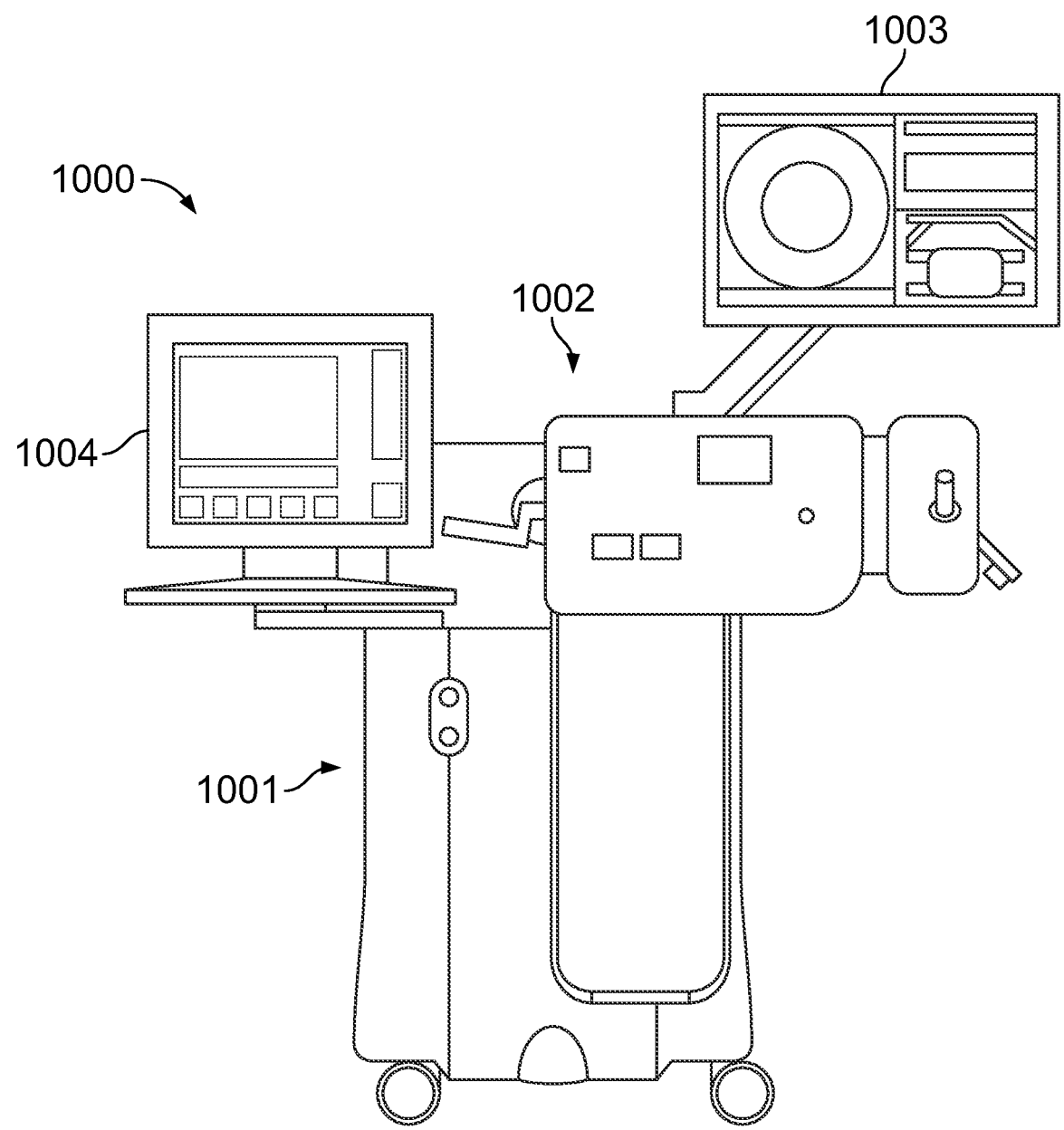
FIG. 10 provides a perspective view of an exemplary integrated system of the inventive concept.

An example of an integrated system of the inventive concept is shown in FIG. 10. As shown, the integrated system 1000 includes a femtosecond laser 1001 (which in some embodiments can include an integrated phacoemulsification system), a first GUI 1004, a second GUI 1003 and a modeling engine 1002. The first GUI 1004 and/or the second GUI 1003 can receive and display information and data. Examples of such information and data include control information, information regarding operation of the system, selections for the user, user input, patient data, modeling information, modeled information, predicted effects, representations, data, tables, as well as representations, images, information and data derived form or generated by the modeling engine 1002.

Figure 11:
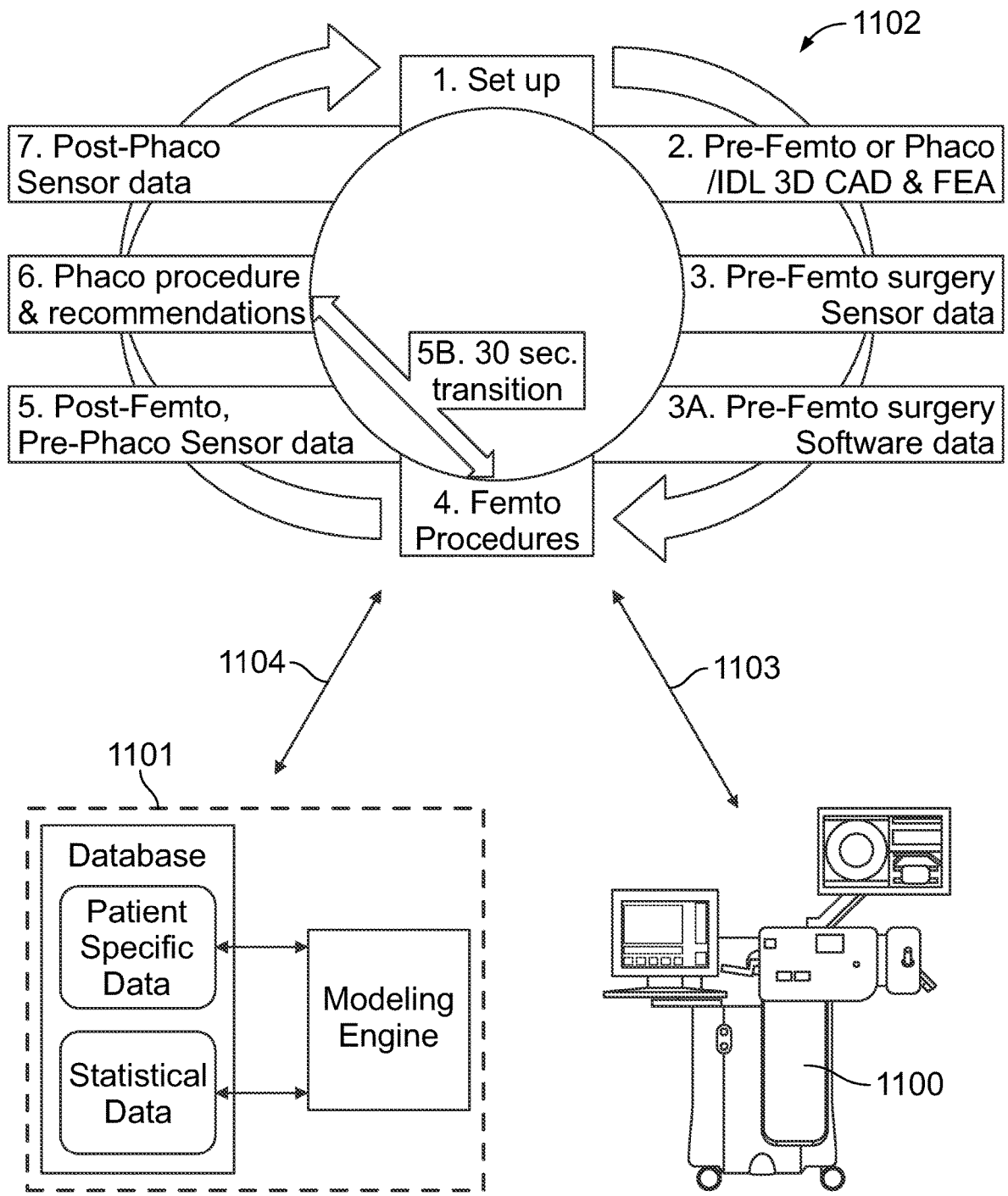
FIG. 11 provides a flow chart and schematic of system workflow and communication.

An illustration of an example of the communication and workflow between a modeling engines and a laser system of the inventive concept is shown in FIG. 11. As shown, a femtosecond laser system 1100 (which in some embodiments includes an integrated phacoemulsification system) and a modeling system 1101 having a modeling engine one or more patient databases (which can include pre- and post-procedure information, and/or a statistical data base), each of which is in communication with the modeling engine. The modeling system 1101 is in communication, and in some embodiments control communication, with the femtosecond laser as shown by arrows 1103 and 1104. An example of the communication and workflow within and between the system 1100 and system 1101 is shown by workflow chart 1102.

At least some or all of the components of the modeling system 1101 can be integral with the laser system 1100 (e.g., contained within a common housing). In some embodiments at least some or all of the components of the modeling system 1101 can be located in a stand-alone unit that is in communication by wireless, network, or wired communication systems with the laser system 1100. In some embodiments of the inventive concept at least some or all of the components of the modeling system 1101, can be located in the cloud. Combinations and various of these configurations are also contemplated.

The workflow charts of FIG. 1, FIG. 2 and the physiomechanical models of the Examples, as well as, combinations and variations of these, can be used the embodiments of shown in FIGS. 10 and 11, as well as, other embodiments of the present systems. Embodiments such laser systems can include a phacoemulsification system that is partially or completely integrated with the laser system, including integration with and communication with the modeling engine.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A system for assisting a user in performance of an ophthalmic surgery on an eye of a patient, comprising:
   a user interface communicatively coupled to an input/output interface, and configured to communicate with a user device;
   a database comprising a patient database, a clinical database, and a procedure database, wherein the database is communicatively coupled to the input/output interface, and
   a processor communicatively coupled to the input/output interface and the database, wherein the processor comprises an algorithm providing a physiomechanical model of the eye or a portion of the eye,
   wherein at least one of the input/output interface, the database, and the processor are cloud-based; and,
   the database comprising additional ophthalmic data for use in generating the physiomechanical model, wherein such data is selected from the group consisting of corneal acoustic response or ultrasound data, topographic data, pachymetric data, elevation data, corneal thickness data, corneal curvature data, wave front data, intraocular pressure data, peripheral stromal thickness data, patient age, patient gender, duration of contact lens use, prior surgical intervention, response to prior surgical intervention, and yield point of a cornea.

2. The system of claim 1, wherein the input/output interface comprises a planning module.

3. The system of claim 1, wherein the input/output interface comprises a treatment module.

4. The system of claim 1, wherein the database comprises a practitioner database.

5. The system of claim 1, wherein the database comprises an instrument database.

6. The system of claim 1, wherein the processor comprises a machine learning algorithm configured to correlate data from the clinical database with data from the patient database, and to provide a treatment recommendation via the input/output interface.

7. A method of assisting a user in performance of an ophthalmic surgery on an eye of a patient, comprising;
    accessing planning module of an input/output interface that is communicatively coupled to a database and a processor, wherein the input/output interface comprises an algorithm assist, and wherein the database comprises a patient database, a clinical database, and a procedure database;
    inputting a desired outcome from the ophthalmic surgery via the input/output interface;
    determining a recommended procedure using a machine learning algorithm of the processor and data from the patient, clinical, and procedure databases; and
    transmitting the recommended procedure to the input/output interface,
    wherein at least one of the input/output interface, the database, and the processor are cloud-based; and,
    the database comprising additional ophthalmic data for use in determining the recommended procedure, wherein such data is selected from the group consisting of corneal acoustic response or ultrasound data, topographic data, pachymetric data, elevation data, corneal thickness data, corneal curvature data, wave front data, intraocular pressure data, peripheral stromal thickness data, patient age, patient gender, duration of contact lens use, prior surgical intervention, response to prior surgical intervention, and yield point of a cornea.

8. The method of claim 7, comprising generating a physiomechanical model of the eye or a portion thereof.

9. The method of claim 8, wherein the desired outcome is inputted by interaction of the user with the physiomechanical model.

10. The method of claim 8, wherein the recommended procedure is communicated to the user via the physiomechanical model.

11. The method of claim 7, wherein the database comprises a practitioner database, and wherein the recommended procedure is determined in part by data from the practitioner database.

12. The method of claim 7, wherein the database comprises an instrument database, and wherein the recommended procedure is determined in part by data from the instrument database.

13. The method of claim 7, comprising transmitting a probable outcome of the recommended procedure to the input/output interface.

14. The method of claim 13, comprising inputting a modification to the recommended procedure based on the probable outcome to generate revised procedure and a revised outcome, and transmitting the revised outcome to the input/output interface when the probable outcome is not acceptable.

15. A method of assisting a user in performance of an ophthalmic surgery on an eye of a patient, comprising:
    physically characterizing the eye to determine at least a first density and at least a first dimension of a structure of the eye;
    applying the determined density(ies) and dimension(s) to derive a physiomechanical model representative of the structure the eye or its anatomy;
    receiving from the user a selection of a selected ophthalmic procedure;
    applying the selected ophthalmic procedure to the physiomechanical model to predict an effect of applying the selected ophthalmic procedure to the structure of the eye; and
    providing the user with a representation of the predicted effect of the selected ophthalmic procedure when applied to the structure of the eye,
    wherein the physiomechanical model is derived from a mechanical property of the eye or a portion thereof within an anatomical context; and,
    comprising acquiring additional ophthalmic data for use in generating the physiomechanical model, wherein such data is selected from the group consisting of corneal acoustic response or ultrasound data, topographic data, pachymetric data, elevation data, corneal thickness data, corneal curvature data, wave front data, intraocular pressure data, peripheral stromal thickness data, patient age, patient gender, duration of contact lens use, prior surgical intervention, response to prior surgical intervention, and yield point of a cornea.

16. The method of claim 15, comprising applying the selected procedure to the eye.

17. The method of claim 15, wherein the representation of the predicted effect is derived from structural analysis of alteration of the mechanical property by the selected procedure.

18. The method of claim 15, wherein the representation of the predicated effect is derived from minimization of a calculated strain or static energy following application of the selected procedure, wherein the calculated strain or static energy is derived from the mechanical property.

19. The method of claim 15, wherein the representation of the predicated effect is derived from an analysis of the eye or the portion thereof as a flexible laminated structure following application of the selected procedure.

20. The method of claim 15, further comprising:
    modifying the selected ophthalmic procedure to generate a modified ophthalmic procedure; and
    using the physiomechanical model to predict a second predicted effect resulting from applying the modified ophthalmic procedure to the eye.

21. The method of claim 20, wherein the second predicted effect on the structure of the eye provides a modified eye structure, and wherein calculated physical characteristics of the modified eye structure are utilized to generate a second physiomechanical model representative of the modified eye structure.

22. A laser system comprising:
    a femtosecond laser for delivering a femtosecond laser beam to an eye;
    a modeling system comprising a modeling engine and a patient data base; the patient data base configured to receive a determined density characterization of a structure of the eye and a determined dimensional characterization of the structure of the eye; and a graphic user interface (GUI), configured to receive an input from a user and display an output from the modeling system; the input comprising a selected procedure, wherein the modeling system is configured to:

derive a physiomechanical model representation of the structure of the eye based upon the determined density characterization of the structure of the eye received by the patient data base, the determined dimensional characterization of the structure of the eye received by the patient data base, or both;

receive from the GUI the selected procedure;

apply the selected procedure to the physiomechanical model representation and thereby derive a predicted effect of the selected procedure on the structure of the eye; and, provide a representation of the predicted effect to the GUI; and comprising the patient data based configured to receive additional ophthalmic data for use in determining the recommended procedure, wherein such data is selected from the group consisting of corneal acoustic response or ultrasound data, topographic data, pachymetric data, elevation data, corneal thickness data, corneal curvature data, wave front data, intraocular pressure data, peripheral stromal thickness data, patient age, patient gender, duration of contact lens use, prior surgical intervention, response to prior surgical intervention, and yield point of a cornea.

23. The system of claim 22, comprising a phacoemulsification system.

24. The systems of claim 22, wherein the selected procedure is a limbus relaxing incision.

25. The systems of claim 22, wherein the selected procedure is a micro-incision in a cornea.

* * * * *